(12) United States Patent
Kelly et al.

(10) Patent No.: US 11,890,352 B2
(45) Date of Patent: Feb. 6, 2024

(54) PLECTIN-TARGETED LIPOSOMES/PARP INHIBITOR IN THE TREATMENT OF CANCER

(71) Applicant: University of Virginia Patent Foundation, Charlottesville, VA (US)

(72) Inventors: Kimberly A. Kelly, Goochland, VA (US); Siva Sai Krishna Dasa, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/971,095

(22) PCT Filed: Feb. 27, 2019

(86) PCT No.: PCT/US2019/019752
§ 371 (c)(1),
(2) Date: Aug. 19, 2020

(87) PCT Pub. No.: WO2019/168921
PCT Pub. Date: Sep. 6, 2019

(65) Prior Publication Data
US 2020/0390903 A1    Dec. 17, 2020

Related U.S. Application Data

(60) Provisional application No. 62/635,676, filed on Feb. 27, 2018.

(51) Int. Cl.
    *A61K 47/69*    (2017.01)
    *A61K 47/62*    (2017.01)
    *A61K 31/282*   (2006.01)
    *A61K 31/337*   (2006.01)
    (Continued)

(52) U.S. Cl.
    CPC ........ *A61K 47/6911* (2017.08); *A61K 31/282* (2013.01); *A61K 31/337* (2013.01); *A61K 31/498* (2013.01); *A61K 31/704* (2013.01); *A61K 47/62* (2017.08)

(58) Field of Classification Search
    CPC .............. A61K 47/6911; A61K 31/282; A61K 31/337; A61K 31/498; A61K 31/704; A61K 47/62
    See application file for complete search history.

(56) References Cited

U.S. PATENT DOCUMENTS

2015/0202315 A1*  7/2015  Wu ........................ A61K 47/62
                                                       424/450
2017/0267719 A1   9/2017  Madamsetty et al.

FOREIGN PATENT DOCUMENTS

| EP | 2862871 A1 | 4/2015 |
| WO | 2006/124836 | * 11/2006 |
| WO | WO-2016205397 A2 | 12/2016 |

(Continued)

OTHER PUBLICATIONS

"International Application Serial No. PCT/US2019/019752, International Preliminary Report on Patentability dated Sep. 3, 2020", 9 pgs.

(Continued)

*Primary Examiner* — Gollamudi S Kishore
(74) *Attorney, Agent, or Firm* — Schwegman Lundberg & Woessner, P.A.

(57) ABSTRACT

The present invention provides compositions and methods to treat cancer.

11 Claims, 17 Drawing Sheets

Specification includes a Sequence Listing.

(51) Int. Cl.
    *A61K 31/498*    (2006.01)
    *A61K 31/704*    (2006.01)

(56)          References Cited

FOREIGN PATENT DOCUMENTS

WO    WO-2017177199 A2    10/2017
WO    WO-2019168921 A1    9/2019

OTHER PUBLICATIONS

"International Application Serial No. PCT/US2019/019752, International Search Report dated Jun. 13, 2019", 6 pgs.
"International Application Serial No. PCT/US2019/019752, Written Opinion dated Jun. 13, 2019", 7 pgs.
Vanna, Sanna, et al., "Targeted Nanoparticles for the Delivery of Novel Bioactive Molecules to Pancreatic Cancer Cells", Journal of Medicinal Chemistry, vol. 59, No. 11, (Jun. 9, 2016), 5209-5220.
Kelly, Kimberly A., "Evaluation of pharmacokinetic and pharmacodynamic profiles of liposomes for the cell type-specific delivery of small molecule drugs", Nanomedicine. Nov. 2017 13(8), (Nov. 2017), 24 pages.
Kelly, Kimberly A., "Plectin-targeted liposomes enhance the therapeutic efficacy of a PARP inhibitor in the treatment of ovarian cancer", Theranostics 2018, vol. 8, Issue 10, (Apr. 11, 2018), 17 pages.

\* cited by examiner

1. UNTREATED (n=5)
2. SYSTEMIC AZ7379 −0.5 (0.5 mg/Kg/DAY) (n=5)
3. SYSTEMIC AZ7379 −1 (1 mg/Kg/DAY) (n=6)
4. NO PEP AZ7379 (1 mg/Kg/DAY) (n=6)
5. NCP AZ7379 (1 mg/Kg/DAY) (n=6)
6. PTP AZ7379 −0.5 (0.5 mg/Kg/DAY) (n=6)
7. PTP AZ7379 −1 (1 mg/Kg/DAY) (n=6)

SYSTEMIC AZ7379 DELIVERED VIA ORAL GAVAGE (3X/WEEK)
NO PEPTIDE OR NCP OR PTP AZ7379 DELIVERED
VIA TAIL VEIN INJECTIONS (2X/WEEK)

1. UNTREATED (n=6)
2. SYSTEMIC AZ7379 (1 mg/Kg/DAY) (n=6)
3. NO PEP AZ7379 (1 mg/Kg/DAY) (n=6)
4. PTP AZ7379 (1 mg/Kg/DAY) (n=6)

SYSTEMIC AZ7379 DELIVERED VIA ORAL GAVAGE (3X/WEEK)
NO PEPTIDE OR NCP OR PTP AZ7379 DELIVERED
VIA TAIL VEIN INJECTIONS (2X/WEEK)

| Properties | AZ7379 |
|---|---|
| pKa | 11.5a, 8.7a, 8.94c |
| Polar surface area $A^2$ | 85.32b |
| Total Area $A^2$ | 667.06b |
| Non-polar area $A^2$ | 587.74b |
| Non-polar/polar | 6.818b |
| Solubility (mM) [pH] | 2.5[7.4]c |
| Charge [pH] | 1.02 [5,6,7,7.4]b |
| pI | 9.72b |
| Log P | 1.89a, 2.75a |
| LogD at pH 7 | 1.05a |
| $t_{1/2}$ - Oral (min) | 55.6 |
| $t_{1/2}$ - i.v (min) | 3.4 |

SEQUENCE LISTING

<160> NUMBER OF SEQ ID NOS: 27

<210> SEQ ID NO 1
<211> LENGTH: 12
<212> TYPE: PRT
<213> ORGANISM: Artificial Sequence
<220> FEATURE:
<223> OTHER INFORMATION: A synthetic amino acid sequence

<400> SEQUENCE: 1

Lys Thr Leu Leu Pro Thr Pro Gly Gly Ser Lys Cys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 2

Lys Thr Leu Leu Pro Thr Pro
1               5

<210> SEQ ID NO 3
<211> LENGTH: 8
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(8)
<223> OTHER INFORMATION: Xaa = Any Amino Acid

<400> SEQUENCE: 3

Xaa Lys Thr Leu Leu Pro Thr Pro
1               5

<210> SEQ ID NO 4
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 4

Xaa Lys Thr Leu Leu Pro Thr Pro Gly Gly Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: A synthetic amino acid sequence

<400> SEQUENCE: 5

Lys Thr Thr Leu Pro Thr Pro Gly Gly Ser
1               5                   10

<210> SEQ ID NO 6
<211> LENGTH: 7
<212> TYPE: PRT
<213> ORGANISM: Artificial Sequence
<220> FEATURE:

```
<223> OTHER INFORMATION: A synthetic amino acid sequence

<400> SEQUENCE: 6

Lys His Val Met Ser Lys Gln
1               5

<210> SEQ ID NO 7
<211> LENGTH: 10
<212> TYPE: PRT
<213> ORGANISM: Artificial Sequence
<220> FEATURE:
<223> OTHER INFORMATION: A synthetic amino acid sequence

<400> SEQUENCE: 7

Lys His Val Met Ser Lys Gln Gly Gly Ser
1               5                   10

<210> SEQ ID NO 8
<211> LENGTH: 8
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(8)
<223> OTHER INFORMATION: Xaa = Any Amino Acid

<400> SEQUENCE: 8

Xaa Lys His Val Met Ser Lys Gln
1               5

<210> SEQ ID NO 9
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 9

Xaa Lys His Val Met Ser Lys Gln Gly Gly Ser
1               5                   10

<210> SEQ ID NO 10
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 10

Ala Thr Leu Leu Pro Thr Pro
1               5

<210> SEQ ID NO 11
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 11

Lys Ala Leu Leu Pro Thr Pro
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 12

Lys Thr Ala Leu Pro Thr Pro
1               5

<210> SEQ ID NO 13
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 13

Lys Thr Leu Ala Pro Thr Pro
1               5

<210> SEQ ID NO 14
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 14

Lys Thr Leu Leu Ala Thr Pro
1               5

<210> SEQ ID NO 15
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 15

Lys Thr Leu Leu Pro Ala Pro
1               5

<210> SEQ ID NO 16
<211> LENGTH: 7
<212> TYPE: PRT
<213> ORGANISM: Artificial Sequence
<220> FEATURE:
<223> OTHER INFORMATION: A synthetic amino acid sequence

<400> SEQUENCE: 16

Lys Thr Thr Leu Pro Thr Ala
1               5

<210> SEQ ID NO 17
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 17

Xaa Ala Thr Leu Leu Pro Thr Pro Gly Gly Ser
1               5                   10
```

```
<210> SEQ ID NO 18
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 18

Xaa Lys Ala Leu Leu Pro Thr Pro Gly Gly Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 19

Xaa Lys Thr Ala Leu Pro Thr Pro Gly Gly Ser
1               5                   10

<210> SEQ ID NO 20
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 20

Xaa Lys Thr Leu Ala Pro Thr Pro Gly Gly Ser
1               5                   10

<210> SEQ ID NO 21
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 21

Xaa Lys Thr Leu Leu Ala Thr Pro Gly Gly Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 22

Xaa Lys Thr Leu Leu Pro Ala Pro Gly Gly Ser
```

```
1               5                    10

<210> SEQ ID NO 23
<211> LENGTH: 11
<212> TYPE: PRT
<213> ORGANISM: Artificial Sequence
<220> FEATURE:
<223> OTHER INFORMATION: A synthetic amino acid sequence
<221> NAME/KEY: VARIANT
<222> LOCATION: (1)...(11)
<223> OTHER INFORMATION: Xaa = Any Amino Acid

<400> SEQUENCE: 23

Xaa Lys Thr Leu Leu Pro Thr Ala Gly Gly Ser
1               5                    10

<210> SEQ ID NO 24
<211> LENGTH: 4
<212> TYPE: PRT
<213> ORGANISM: Artificial Sequence
<220> FEATURE:
<223> OTHER INFORMATION: A synthetic amino acid sequence

<400> SEQUENCE: 24

Lys Lys Lys Lys
1

<210> SEQ ID NO 25
<211> LENGTH: 12
<212> TYPE: PRT
<213> ORGANISM: Artificial Sequence
<220> FEATURE:
<223> OTHER INFORMATION: A synthetic amino acid sequence

<400> SEQUENCE: 25

Thr Ala Leu Pro Arg Leu Asn Gly Gly Ser Lys Cys
1               5                    10

<210> SEQ ID NO 26
<211> LENGTH: 18
<212> TYPE: PRT
<213> ORGANISM: Artificial Sequence
<220> FEATURE:
<223> OTHER INFORMATION: A synthetic amino acid sequence

<400> SEQUENCE: 26

Ala Lys Thr Leu Leu Pro Thr Pro Gly Gly Ser Lys Lys Lys Asp Thr
1               5                    10                   15

Ala Ala

<210> SEQ ID NO 27
<211> LENGTH: 15
<212> TYPE: PRT
<213> ORGANISM: Artificial Sequence
<220> FEATURE:
<223> OTHER INFORMATION: A synthetic amino acid sequence

<400> SEQUENCE: 27

Lys Thr Leu Leu Pro Thr Pro Gly Gly Ser Lys Cys Met Ala Leu
1               5                    10                   15
```

PLECTIN-TARGETED LIPOSOMES/PARP INHIBITOR IN THE TREATMENT OF CANCER

CLAIM OF PRIORITY

This application is a U.S. National Stage Filing under 35 U.S.C. § 371 from International Application No. PCT/US2019/019752, filed on 27 Feb. 2019, which claims the benefit of priority of U.S. Provisional Patent Application No. 62/635,676, filed on 27 Feb. 2018, the benefit of priority of which are claimed hereby, and which are incorporated by reference herein in their entireties.

GOVERNMENT GRANT SUPPORT

This invention was made with government support under Grant No. CA168712 awarded by the National Institutes of Health. The government has certain rights in the invention.

BACKGROUND OF THE INVENTION

Individuals that harbor mutations in BRCA1/2 proteins that play a role in the repair of double-stranded DNA breaks induced during homologous recombination, have a high risk for breast, pancreas or ovarian cancers (7,8). Ovarian cancer is commonly associated with homologous recombination (HR) deficiency resulting from BRCA1/2 (10-20% of high grade ovarian cancers) and BRCA-like mutations (50% of high grade ovarian cancers) (9-11) which make them sensitive to agents such as PARP inhibitors that prevent DNA repair (12). The US Food and Drug Administration (FDA) recently approved the use of PARP inhibitors (Olaparib, Niraparib and Rucaparib) in the population with BRCA1/2 mutations for treatment of ovarian cancer patients with platinum-sensitivity and recurrent ovarian cancer (13-15). However, 10% of the patients showed adverse side effects, such as the life-threatening conditions of neutropenia and thrombocytopenia, when given the doses necessary to achieve PARP inhibition (12,16-19). About 2% of patients who received Olaparib developed myelodysplastic syndrome and acute myeloid leukemia resulting from excessive PARP inhibition in the bone marrow (20), indicating that off-target effects were substantial in these patients.

SUMMARY OF THE INVENTION

One embodiment provides a composition comprising a Plectin Targeted Peptide (PTP) conjugated-nanoparticle, wherein the PTP is on the surface of the nanoparticle and the nanoparticle encapsulates a payload. In one embodiment, the PTP is any one of SEQ ID NOs: 1-24. In another embodiment, the PTP is SEQ ID NO: 1. In one embodiment, the nanoparticle is a liposome. In one embodiment, the payload is an anticancer compound, such as carboplatin, doxorubicin or paclitaxel or a PARP inhibitor, including AZ7379.

One embodiment provides a method to treat cancer comprising administrating to a subject in need thereof an effective amount of any one of the compositions described herein. In one embodiment, the cancer expresses plectin (UniProtKB-Q15149 (PLEC_HUMAN); Gene ID: 5339(uid)). In another embodiment, the cancer has a BRAC1/2 mutation. In one embodiment, the cancer is ovarian cancer.

One embodiment provides a method to decrease tumor volume comprising administering to a subject in need thereof an effective amount of any one of the compositions described herein. Another embodiment provides a method to decrease tumor growth comprising administering to a subject in need thereof an effective amount of any one of the compositions described herein. Another embodiment provides a method to increase the efficacy of a PARP inhibitor comprising encapsulating the PARP inhibitor in the nanoparticle of any one of the compositions described herein.

DETAILED DESCRIPTION OF THE INVENTION

Figure 1A:
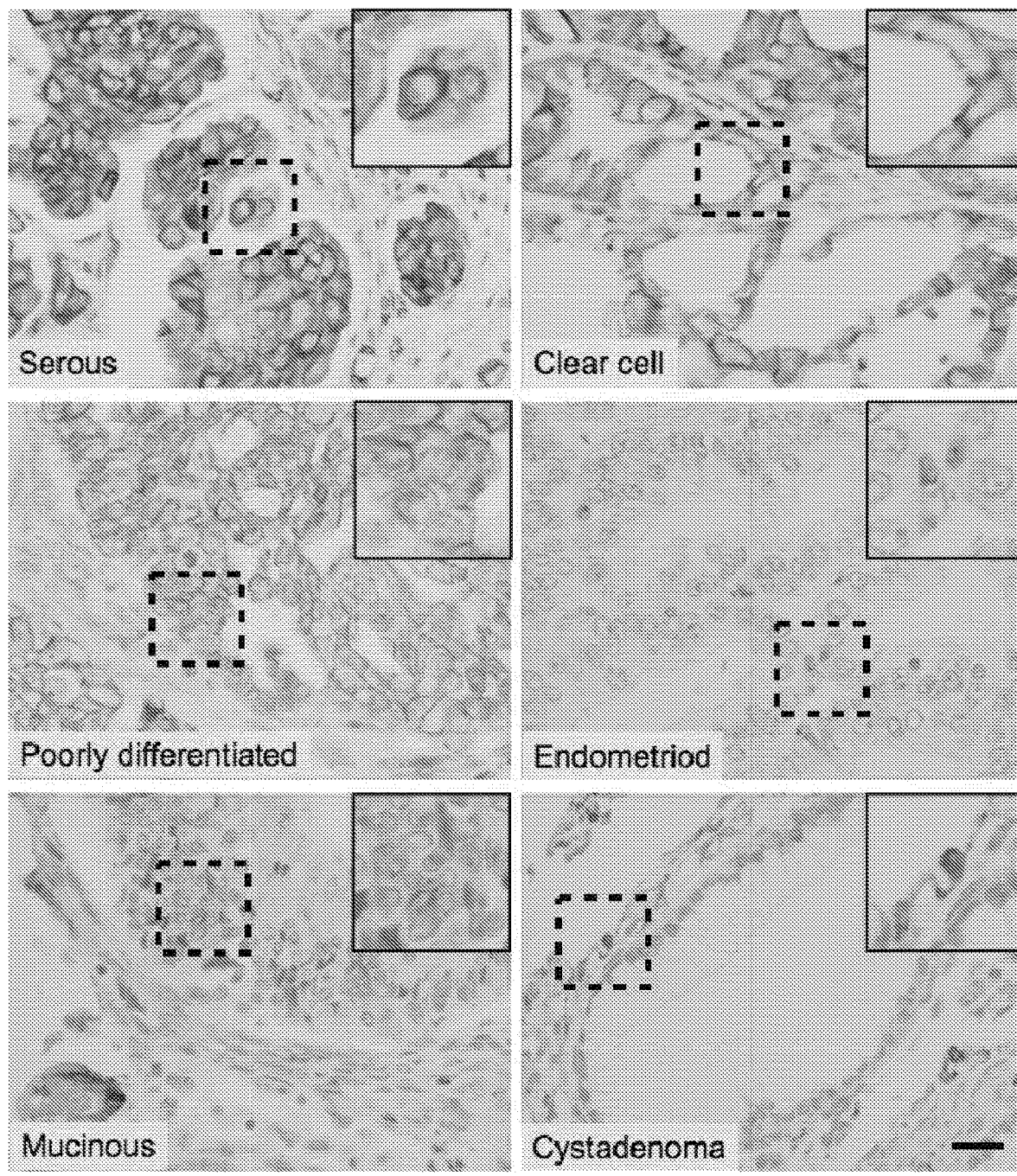
FIGS. 1A-C provide representative images of Plectin-1 Immunohistochemistry of Ovarian TMAs. A) Representative images of serous, clear cell, poorly differentiated, mucinous, and endometrioid carcinomas and benign cystadenoma tumors. In serous, clear cell and poorly differentiated carcinomas, plectin was highly expressed and localized mostly in the cell membrane. In endometrioid and mucinoius carcinomas, plectin was mostly localized in the cytosol. In benign samples (serous and mucinous cystadenoma), plectin expression was low and localized in the cytosol. Insets in the images are magnified regions from the corresponding black squares. (Scale bar; 20 µm) B) Western blot for plectin and cell membrane protein, alpha 1 sodium potassium ATPase (ATP1A1) from surface biotinylated fraction of proteins from FT132, SKOV3 and OVCAR8 cells. C) Densitometric ratios of plectin to ATP1A1 were plotted for FT132, SKOV3 and OVCAR8 to determine plectin expression in relation to ATP1A1. (* represents p<0.05).

Advances in genomics and proteomics drive precision medicine by providing actionable genetic alterations and molecularly targeted therapies, respectively. While genomic analysis and medicinal chemistry have advanced patient stratification with treatments tailored to the genetic profile of patient's tumor, proteomic targeting has the potential to enhance therapeutic index of drugs like Poly (ADP-ribose) polymerase (PARP) inhibitors. PARP inhibitors in breast and ovarian cancer patients with BRCA1/2 mutations have shown promise. About 10% of the patients who received Olaparib (PARP inhibitor) showed adverse side effects including neutropenia, thrombocytopenia and in some cases resulted in myelodysplastic syndrome, indicating that off-target effects were substantial in these patients. Through proteomic analysis, plectin, a cytolinker protein that mislocalized onto the cell surface during malignant transformation of healthy ovarian tissue, was previously identified. This cancer specific phenotype allowed one to image pancreatic cancer successfully using Plectin Targeted Peptide (PTP) conjugated to nanoparticles or displayed on capsid protein of Adeno Associated Virus (AAV) particles. Plectin expression and localization in human ovarian tumor specimens were analyzed followed by in vitro confirmation of cell surface plectin localization in healthy and ovarian cancer cell lines. PTP conjugated liposomes were prepared and their specificity for plectin+ cells determined in vitro and in vivo. A remote loading method was employed to encapsulate a PARP inhibitor (AZ7379) into liposomes. Ideal buffer exchange method and remote loading conditions were determined based on the amount of lipid and drug recovered at the end of remote loading process. Finally, in vivo tumor growth studies were performed to determine the efficacy of PTP liposomes in preventing PARP activity in mice bearing OVCAR8 (high grade epithelial ovarian cancer (EOC)) tumors.

PTP liposomal AZ7379 delivery not only enhanced PARP inhibition but also resulted in decelerated tumor growth in mice bearing subcutaneous and intraperitoneal OVCAR8 tumors. In mice bearing subcutaneous or intraperitoneal tumors, treatment with PTP liposomes resulted in a 3- and 1.7-fold decrease in tumor volume, respectively, compared to systemic drug treatment.

Targeted drug delivery assisted by genomic and proteomic data provides an adaptable model system that can be extended to effectively treat other cancers and diseases.

For the purposes of clarity and a concise description, features can be described herein as part of the same or separate embodiments; however, it will be appreciated that the scope of the invention may include embodiments having combinations of all or some of the features described.

Abbreviations

PARP, poly (ADP-ribose) polymerase; PAR, poly (ADP-ribose); PK, pharmacokinetics; PD, pharmacodynamics; ROI, region of interest; FMT, fluorescence molecular tomography; AUC, area under the curve; DiR, 1,1'-dioctadecyl-3, 3, 3', 3'-tetramethylindotricarbocyanine iodide; FAM, 5(6)-carboxyfluorescein.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment," "an embodiment," etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is di-substituted.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of."

As used herein, the terms "including," "includes," "having," "has," "with," or variants thereof, are intended to be inclusive similar to the term "comprising."

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group.

Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating," "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit," "inhibiting," and "inhibition" refer to the slowing, halting, or reversing the growth or progression of a disease, infection, condition, group of cells, protein or its expression. The inhibition can be greater than about 20%, 40%, 60%, 80%, 90%, 95%, or 99%, for example, compared to the growth or progression that occurs in the absence of the treatment or contacting.

A "targeting molecule" or "targeting agent" is a peptide or other molecule that binds to a targeted component. Optionally, the binding affinity of the targeting molecule may be in the range of 1 nM to 1 µM. In some embodiments, the targeting molecule may be an antagonist of a receptor on the surface of a targeted cell.

A "therapeutic agent," "active agent," or "drug" refers to any molecule used in the treatment, cure, prevention, or diagnosis of a disease or other medical condition. Examples of therapeutic agents include, but are not limited to, FDA-approved drugs, experimental drugs, antibiotics, and nucleic acids (e.g., siRNA, DNA).

As used herein, a "nanoparticle" refers to a micelle or liposome. A delivery vehicle can mean the vehicle alone or one loaded with a therapeutic and/or a diagnostic agent and/or also comprising a targeting peptide of SEQ ID NOs.: 1-24 or related thereto (e.g., 95% identity).

The term lipid includes mono-, di- and triacylglycerols, phospholipids, free fatty acids, fatty alcohols, cholesterol, cholesterol esters, and the like.

The term "phospholipid" as used herein refers to a glycerol phosphate with an organic head-group such as choline, serine, ethanolamine or inositol and zero, one or two (typically one or two) fatty acids esterified to the glycerol backbone. Phospholipids include, but are not limited to, phosphatidylcholine, phosphatidylethanolamine, phosphatidylserine and phosphatidylinositol as well as corresponding lysophospholipids.

The terms "active agent," "therapeutic agent," "drug," and the like, are readily recognized by those of kill in the art. The micelles and liposomes described herein can encapsulate various drugs, such as those drugs exemplified in the description herein, or another therapeutic or otherwise active agent known in the art.

The terms "cell," "cell line," and "cell culture" as used herein may be used interchangeably. All of these terms also include their progeny, which are any and all subsequent generations. It is understood that all progeny may not be identical due to deliberate or inadvertent mutations.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, including at least about 75%, at least about 90%, or at least about 95% of the nucleotide residues of the first portion are capable of base pairing with nucleotide residues in the second portion.

In some embodiments, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC5' share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

As an example of linker technology, see Bausch et al. Clin Cancer Res. 2011 Jan. 15; 17(2): 302-309; in which the Tetramericplectin-1-targeted peptide (tPTP-4 (βAKTLLPTPGGS(PEG5000))KKKDOTAβA-NH2)) (SEQ ID NO: 26) was synthesized. In other words, four plectin-targeted peptides (PTPs) were tied to a single DOTA chelator by (4) PEG5000 linkers. The DOTA, of course, then binds a payload, such as therapeutic drug or diagnostic (e.g., radioactive element needed for imaging). See also U.S. Pat. No. 9,623,128.

Spacers are also of use in the invention, such as a PEG spacer.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "otherwise identical sample," as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "peptide" typically refers to short polypeptides.

As used herein, the term "peptide ligand" (or the word "ligand" in reference to a peptide) refers to a peptide or fragment of a protein that specifically binds to a molecule, such as a protein, carbohydrate, and the like. A receptor or binding partner of the peptide ligand can be essentially any type of molecule such as polypeptide, nucleic acid, carbohydrate, lipid, or any organic derived compound. Specific examples of ligands are peptide ligands of the present inventions (e.g., those in SEQ ID NOs.: 1-24).

As used herein, the term "pharmaceutically-acceptable carrier" means a chemical composition with which an appropriate compound or derivative can be combined and which, following the combination, can be used to administer the appropriate compound to a subject. "Pharmaceutically acceptable" means physiologically tolerable, for either human or veterinary application. As used herein, "pharmaceutical compositions" include formulations for human and veterinary use.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., The Peptides, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "providing a prognosis" refers to providing information regarding the impact of the presence of cancer (e.g., as determined by the diagnostic methods of the present invention) on a subject's future health.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest. By "small interfering RNAs (siRNAs)" is meant, inter alia, an isolated dsRNA molecule comprised of both a sense and an anti-sense strand. In one aspect, it is greater than 10 nucleotides in length.

siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

By the term "specifically binds to," as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

As used herein, a "subject in need thereof" is a patient, animal, mammal, or human, who will benefit from the method of this invention.

As used herein, a "substantially homologous amino acid sequences" includes those amino acid sequences which have at least about 95% homology, at least about 96% homology, at least about 97% homology, at least about 98% homology, or at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997

Nucleic Acids Res. 25:3389-3402). The default settings provided with these programs are suitable for determining substantial similarity of nucleic acid sequences for purposes of the present invention.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22: 1859-1862, 1981, and Matteucci et al., J. Am. Chem. Soc. 103:3185, 1981.

Targeting Peptides

Plectin Targeting Peptide—PTP

PTPs include, but are not limited to, the following amino acid sequences:

KTLLPTPGGSK(FAM)C (SEQ ID NO: 1);
Lys Thr Leu Leu Pro Thr Pro (SEQ ID NO: 2);
Xaa Lys Thr Leu Leu Pro Thr Pro (SEQ ID NO: 3;
Xaa Lys Thr Leu Leu Pro Thr Pro Gly Gly Ser (SEQ ID NO: 4);
Lys Thr Thr Leu Pro Thr Pro Gly Gly Ser (SEQ ID NO: 5);
Lys His Val Met Ser Lys Gln (SEQ ID NO: 6);
Lys His Val Met Ser Lys Gln Gly Gly Ser (SEQ ID NO: 7);
Xaa Lys His Val Met Ser Lys Gln (SEQ ID NO: 8);
Xaa Lys His Val Met Ser Lys Gln Gly Gly Ser (SEQ ID NO: 9);
Ala Thr Leu Leu Pro Thr Pro (SEQ ID NO: 10);
Lys Ala Leu Leu Pro Thr Pro (SEQ ID NO: 11);
Lys Thr Ala Leu Pro Thr Pro (SEQ ID NO: 12);
Lys Thr Leu Ala Pro Thr Pro (SEQ ID NO: 13);
Lys Thr Leu Leu Ala Thr Pro (SEQ ID NO: 14);
Lys Thr Leu Leu Pro Ala Pro (SEQ ID NO: 15);
Lys Thr Thr Leu Pro Thr Ala (SEQ ID NO: 16);
Xaa Ala Thr Leu Leu Pro Thr Pro Gly Gly Ser (SEQ ID NO: 17);
Xaa Lys Ala Leu Leu Pro Thr Pro Gly Gly Ser (SEQ ID NO: 18);
Xaa Lys Thr Ala Leu Pro Thr Pro Gly Gly Ser (SEQ ID NO:19);
Xaa Lys Thr Leu Ala Pro Thr Pro Gly Gly Ser (SEQ ID NO: 20);
Xaa Lys Thr Leu Leu Ala Thr Pro Gly Gly Ser (SEQ ID NO: 21);
Xaa Lys Thr Leu Leu Pro Ala Pro Gly Gly Ser (SEQ ID NO: 22);
Xaa Lys Thr Leu Leu Pro Thr Ala Gly Gly Ser (SEQ ID NO: 23); and/or
Lys Lys Lys Lys (SEQ ID NO: 24).

The Plectin Targeting Peptides (PTPs) provided herein can be prepared by well-known synthesis schemes. The peptides encompass those peptide sequences provided herein and those that have one or more substitutions, deletions and/or additions as compared to the sequences provided herein (such as those that comprise 1 or 2 substitutions, deletions and/or additions). The peptides may encompass one or more substitutions, such as conservations substitutions. They also encompass deletions and additions of one or more amino acids and non-natural amino acids. For example, the targeting peptide consists of about 5 to about 25 amino acids or about 3 to about 7, including 5, 6 and/or 7 amino acids. At least a portion of the amino acid sequence of the targeting peptide is homologous (identical) to at least 3, 4 or 5 consecutive amino acids of those peptides found in SEQ ID NOs: 1-24.

One or more targeting peptides can be used in the practice of the invention herein. Multiple targeting peptides of the same or different sequence can be encompassed in a formulation. Peptides other than targeting peptides can also be included. These peptides include, but are not limited to, peptides with membrane penetrating functions, nuclear targeting functions, cytosolic targeting functions, and/or endosome dissolution function (TAP peptide; buffering compounds added to the liposome compositions (polyethylamine) to burst endosome).

The peptides can be extended away from the delivery vehicle (e.g., liposome) via the use of a chain extender, such as a PEG chain extender/spacer, so that the peptide is extended away from, for example, the liposomal surface.

In one embodiment, one or more peptides are conjugated directly or indirectly via a spacer or linker molecule to a payload and optionally includes a delivery vehicle.

As used herein, amino acids are represented by the full name thereof, by the three-letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |

| Full Name | Three-Letter Code | One-Letter Code |
| --- | --- | --- |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity (e.g., peptidomimetic for making peptides protease resistant). Additionally, a disulfide linkage may be present or absent in the peptides of the invention.

Amino acids have the following general structure:

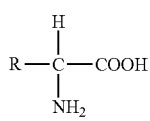

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, the term "conservative amino acid substitution" is defined herein as an amino acid exchange within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln;
III. Polar, positively charged residues:
   His, Arg, Lys;
IV. Large, aliphatic, nonpolar residues:
   Met Leu, Ile, Val, Cys
V. Large, aromatic residues:
   Phe, Tyr, Trp Embodiments of this application relate to cancer targeting peptides that are selective for cancer cells. The targeting peptide consists of about 5 to about 25 amino acids or about 3 to about 7, including 5, 6 and/or 7 amino acids. At least a portion of the amino acid sequence of the targeting peptide is homologous (identical) to at least 3, 4 or 5 consecutive amino acids of those peptides found in SEQ ID NOs.: 1-24.

In some embodiments, the targeting peptides described herein includes an amino acid sequence of one or more of those presented in SEQ ID NOs.: 1-24. In other embodiments, the targeting peptide has an amino acid sequence that consists of a sequence found in SEQ ID NOs.: 1-24. The targeting peptide can be targeted to and selectively bind to cancer tissue when administered to a subject. The targeting peptide can bind to the cancer tissue with a higher affinity than non-cancer tissues.

A targeting peptide of the present invention can be synthesized using any well-known method previously described. Following peptide synthesis, peptides can be analyzed to insure proper synthesis. For example, proper synthesis can be confirmed using mass spectrometry and/or purity of the peptides can be verified using reverse phase liquid chromatography.

Delivery Vehicles

Delivery vehicles are those formulations which in combination with the targeting peptides disclosed herein deliver the payload (e.g., therapeutic drug, protein or diagnostic compound) to a tumor cell, such as an ovarian tumor cell. The formulations can include, but are not limited to, liposomes, micelles, non-liposomal nanoparticles, nanoparticles made of drug, microbubbles, nanoparticles of polymer, metal oxide and/or lipid, dendrimers, and/or adeno-associated virus (AAV) vectors. Essentially any type of formulation that can be used to deliver a payload can be made to be specific with the selective approach discussed herein (the use of a peptide of SEQ ID NOs.: 1-24 to target cancer cells). Thus, term "delivery vehicle" refers to the vehicle itself, such as a liposome or an AAV vector, and also refers to a vehicle loaded with a payload (e.g., a pharmaceutic or diagnostic) and associated with targeting peptides.

Liposomes and Micelles

A liposome is a spherical vesicle having at least one lipid bilayer. Liposomes are most often composed of phospholipids, especially phosphatidylcholine, but may also include other lipids, such as egg phosphatidylethanolamine, so long as they are compatible with lipid bilayer structure. A liposome can include any suitable polymer, such as polymers that are currently in use or are being developed for controlled drug delivery in vivo. For example, the biodegradable polymer can be a polyester, a polylactone, a polycarbonate, a polyamide, or a polyol. The polyester can include of poly(lactic acid), commonly known as PLA, poly (glycolic acid), commonly known as PGA, and their copolymers, commonly known as poly(lactic-co-glycolic) acid or PLGA. Nanoparticles composed of PLGA can have any ratio of PLA and PGA, e.g., a lactic acid:glycolic acid ratio (e.g., molar ratio) of about 95:5 to about 5:95, such as about 75:25 to about 25:75, including about 50:50. The PLGA copolymer can be a random copolymer or block copolymer of lactic acid and glycolic acid. The block copolymers can have 2, 3, 4, or more blocks of PLA and PGA. The lactic acid component can be racemic, enantiomerically enriched with the D or the L isomer, or enantiopure. A liposome design may employ surface ligands (e.g., targeting peptides) for attaching to unhealthy tissue.

The major types of liposomes are the multilamellar vesicle (MLV, with several lamellar phase lipid bilayers), the small unilamellar liposome vesicle (SUV, with one lipid bilayer), the large unilamellar vesicle (LUV), and the cochleate vesicle.

Liposome formation technology is well established in the art (liposomes can be created by sonicating a dispersion of amphipatic lipids, such as phospholipids, in water; they can also be created by other methods including, but not limited to, extrusion and Mozafari method). The liposomes can be prepared in any manner depending on the nature of components to be included. For example, the preparation methods for biodegradable microparticles can be used to prepare the liposomes of the invention. Most preparations are based on solvent evaporation or extraction techniques (see, for example, D. H. Lewis "Controlled Release of Bioactive Agents from Lactide/Glycolide Polymers" in Biodegradable Polymers as Drug Delivery Systems, Marcel Dekker, p. 1 (1990)). The simplest methods involve dissolving the polymer in an appropriate organic solvent and suspending this solution in an aqueous continuous phase which contains an appropriate surfactant. Continuous stirring then allows for evaporation of the organic solvent and hardening of the microparticles. The factors that control the size and size distribution of these particles are the polymer concentration in the solvent, the amount and type of surfactant, and the stirring rate. The solvents used in these techniques can include dichloromethane, acetone, methanol, ethyl acetate, acetonitrile, chloroform, and carbon tetrachloride.

In general, the inventive liposomes can be prepared by combining at least one of the inventive peptides, e.g., one or more peptides provided in SEQ ID NOs.: 1-24, and other components of the liposome, such as phospholipids, in water to form a solution, and then manipulating the solution to form the liposome. Phospholipids suitable for use in the present invention can be natural phospholipids and/or can be purchased from commercial sources.

Micelles are also useful in the present invention.

In addition, the delivery vehicle can include additional components including hydrophobic or hydrophilic drugs, encapsulated in the micelle or liposome interior, or in the liposome bilayer. Various drugs conjugated to PEG or a lipid, such as a phospholipid, can also be incorporated into the nanoparticles (either as a cargo molecule or conjugated to a lipid).

The delivery vehicles include targeting molecules on their surfaces, such as those provided in SEQ ID NOs.: 1-24 or derivative thereof. The peptides can be conjugated to the delivery vehicle in a two-step process. In the first step, the surfaces of the delivery vehicle are activated by suspending the delivery vehicles in borate buffer (50 mM, pH 5.0) by sonication for 30 sec on an ice bath. This is followed by the addition of DENACOL (40 mg), an epoxy that helps conjugation of the peptide on the surface, and the catalyst zinc tetrahydrofluroborate hydrate (50 mg), which are dissolved in an equal volume of buffer to the nanoparticle solution. This mixture can be stirred gently for example, for 30 minutes at 37° C. Delivery vehicles can then be separated by ultracentrifugation for example at 30000 rpm for 20 minutes at 4° C. Any unreacted DENACOL can be removed by multiple wash steps.

In the second step, the peptide can be conjugated to the surface of the activated delivery vehicles by suspending the delivery vehicles in borate buffer (4 ml) and stirring into a solution containing an amount of the targeting peptides in borate buffer. This reaction can be carried out, for example, for 2 hours at 37° C. The unreacted peptide can then be removed by ultracentrifugation and the final delivery vehicle suspension can be lyophilized for 48 hours.

In various embodiments, the invention provides pharmaceutical compositions comprising a plurality of delivery vehicles and a pharmacologically acceptable excipient. The delivery vehicle may have a therapeutic agent coupled to the outer portion of the particle, as well as a targeting agent coupled to the surface. Administration of drug loaded, or drug conjugated delivery vehicles can treat cancer conditions/cells by contacting the tissue or cells and being taken up by the cells and degrading to release the therapeutic agent(s).

For example, one embodiment relates to a method of delivering one or more active agents (e.g., a therapeutic and/or a diagnostic agent) to cancerous tissue of a subject. Systemic delivery of agents contained within a polymeric carrier nanoparticle conjugated to a targeting peptide having one or more sequences as provided in SEQ ID NOs.: 1-24 enhances the uptake of the agents into cells of the cancerous tissue. It is contemplated that encapsulating a therapeutic and/or diagnostic agent of interest into a delivery vehicle (e.g., a PLGA polymeric nanoparticle) tagged with a targeting peptide can provide a targeting encapsulated active agent capable of homing to the cancerous tissue upon systemic administration to a subject. The targeting peptide, when conjugated to a delivery vehicle, such as a polymeric complex can direct the delivery vehicle (e.g., polymeric carrier nanoparticle composition) to the cancerous tissue. The delivery vehicle, such as the polymer, can then release the encapsulated active agent(s) into the area of the cancer. Thus, a delivery vehicle described herein can be used in a method of delivering a therapeutic and/or diagnostic agent to cancerous tissue of a subject. In some embodiments the composition is administered systemically.

A nanoparticle/delivery vehicle composition described herein can include a polymeric carrier and a therapeutic and/or diagnostic agent. Delivery vehicles can generally entrap or encapsulate the therapeutic and/or diagnostic agent in a stable and reproducible manner. The delivery vehicle composition is conjugated to a cancer tissue targeting peptide described herein consisting of about 5 to about 25 amino acids or about 3 to about 7, including 5, 6 and/or 7 amino acids. At least a portion of the amino acid sequence of the cancer tissue targeting peptide is homologous (identical) to at least 3, 4 or 5 consecutive amino acids of those peptides found in SEQ ID NOs.: 1-24.

In some embodiments, the nanoparticle can be a particle of approximately spherical shape measuring less than about 1000 nm in diameter. In one embodiment, the nanoparticles can have a diameter of about 10 nm to about 1000 nm. In another embodiment, the nanoparticles can have a diameter of about 50 to about 500 nm, such as from about 100 to about 400 nm, and including from about 100 to about 250 nm.

Payload

A therapeutic or diagnostic agent, termed herein as a payload, delivered by a delivery vehicle can be any compound, agent or mixture. In some embodiments, the therapeutic agent includes one or more drugs (e.g., small molecules), proteins, peptides, cytokines, nucleic acids (including a gene coding for a protein), RNA, including shRNA, iRNA, microRNAs and/or antagomiRs, hormones, steroids, enzymes or mixtures thereof. Drugs useful in the invention may, for example, possess a pharmaceutical property selected from the group consisting of antimitotic, antikinase, alkylating, antimetabolite, antibiotic, alkaloid, antiangiogenic, pro-apoptotic agents and combinations thereof, including PARP inhibitors, such as PARP-1 (Poly(ADP-ribose) polymerase 1) inhibitor AZ7379.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies.

Gene Therapy

Gene therapy is a viable therapeutic regimen for many conditions. Originally, gene therapy was aimed at partial or total replacement of a diseased or mutated gene, and, thus, at reducing the pathological manifestations of this gene. In recent years a number of models for gene therapy against various pathological manifestations have been presented. These include gene replacement, gene therapy and oligonucleotide therapy (Brigham et al., 1993, Rosenecker et al., 1998). Several approaches for DNA transfection vectors have been used including various viruses' vectors and bacterial plasmid DNA (see review by Schreier, 1994).

The plasmid DNA transfection approach, using liposomes as the gene delivery system, has several advantages, especially when only transient (days or weeks) treatment is required. Among the advantages are convenience of use; pharmaceutical universality; safety (no viral structure is included, and the natural phospholipids are non-immunogenic, a repeated administration can be safe for use as required); and shelf life (gene encapsulated liposomes can be lyophilized to achieve a prolonged shelf life (Allon et al., 1997). In addition, the bacterial plasmid DNA does not integrate with the host genome, and, thus, is not limited to a specific cell. This transient effect provides better control over the degree and duration of the expression.

The ability to prepare vectors/plasmids is known in the art.

In another embodiment, the therapeutic payload is an antisense oligonucleotide. As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

Of course, delivery vehicle, such as liposomes or micelles may include combinations of various encapsulated drugs, diagnostic compounds and various drug-conjugated lipids in their various compositions and formulations.

Diagnostic

A diagnostic agent included with the delivery vehicle or conjugated to a peptide of the invention can include any diagnostic agent used for in vivo contrast imaging and other imaging modalities used to provide contrast tissue.

Diagnostic agents include rare earth metals such as manganese, ytterbium, gadolinium, europium, as well as irons, fluorophores (fluorescein, dansyl, quantum dots, and fluorocarbons).

Radionuclides are also useful both as diagnostic and therapeutic agents. Typical diagnostic radionuclides include 99mTc, 95Tc, mIn, 62Cu, 64Cu, 67Ga and 68Ga, and therapeutic nuclides include 186Re, 188Re, 153Sm, 166Ho, 177Lu, 149Pm, 90Y, 212Bi, 103Pd, 109Pd, 159 Gd, 140La, 198Au 199Au, 169Yb, 175Yb, 165Dy, 166Dy, 67Cu, 105Rh, mAg, and 192 Ir. Means to attach various radioligands to the delivery vehicles of the invention are understood in the art.

The therapeutic and/or diagnostic agent and delivery vehicle may be combined in a number of different ways depending upon the application of interest. For example, the therapeutic and/or diagnostic agent may be non-covalently associated with the delivery vehicle, e.g., nanoparticle, may be coupled to the delivery vehicle, e.g., nanoparticle, or may be coupled to the delivery vehicle, e.g., nanoparticle through spacer moieties or may not contain a delivery vehicle be associated with the peptide (optionally with a vehicle).

Pharmaceutical Formulations

The delivery vehicles described herein can be used to prepare therapeutic pharmaceutical compositions, for example, by combining the delivery vehicles with a pharmaceutically acceptable diluent, excipient, or carrier. The delivery vehicles described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The delivery vehicles described herein may be systemically administered in combination with a pharmaceutically acceptable vehicle, such as an inert diluent or an assimilable edible carrier. For oral administration, delivery vehicles can be enclosed in hard or soft-shell gelatin capsules, compressed into tablets, or incorporated directly into the food of a patient's diet. Delivery vehicles may also be combined with one or more excipients and used in the form of ingestible tablets, buccal tablets, troches, capsules, elixirs, suspensions, syrups, wafers, and the like. Such compositions and preparations typically contain at least 0.1% of the delivery vehicles. The weight percentage of the delivery vehicles in the preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the delivery vehicles may be incorporated into sustained-release preparations and devices. The delivery vehicles may be administered intravenously or intraperitoneal by infusion or injection. Solutions of the delivery vehicles can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the delivery vehicles for the extemporaneous preparation of sterile injectable or infusible solutions or dispersions. The ultimate dosage form for injection or infusion should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the delivery vehicles in the required amount in the appropriate solvent or carrier with various other ingredients enumerated above, as required, optionally followed by filter sterilization. In the case of sterile powders for the preparation of sterile injectable solutions, methods of preparation can include vacuum drying and freeze-drying techniques, which yield a powder of the delivery vehicles plus any additional desired ingredient present in the composition.

For topical administration, delivery vehicles may be applied in pure form or as a solution. However, it will generally be desirable to administer the delivery vehicles to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which delivery vehicles can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the delivery vehicles described herein where an ingredient of such compositions can optionally be replaced by a compound or composition described herein, or a compound or composition described herein can be added to the composition.

Useful dosages of the delivery vehicles described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of delivery vehicles required for use in treatment will vary not only with the particular active compound of the delivery vehicles but also with the route of administration, the nature of the condition being treated, and the age and condition of the patient, and will be ultimately at the discretion of an attendant physician or clinician.

The active compound of the delivery vehicles can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Delivery vehicles, e.g., nanoparticles, loaded with a therapeutic and/or diagnostic agent conjugated to cancer tissue targeting peptides can be administered systemically at a dose ranging from 10 µg of nanoparticles to 100 g of nanoparticles.

The delivery vehicles described herein can be effective in cancer treatments and have higher potency and/or reduced toxicity as compared to the corresponding free active drug. The invention provides therapeutic methods of treating cancer in a mammal, which involve administering to a mammal having cancer an effective amount of a delivery vehicle composition described herein. A mammal includes a primate, human, rodent, canine, feline, bovine, ovine, equine, swine, caprine, bovine and the like.

Treatment of Cancer

The invention further provides methods for delivering a drug or other therapeutic to a cancer cell/tissue, such as ovarian cancer, for example, in a patient. The invention also provides methods for treating cancer in a patient. The methods can include contacting a cancer cell/tissue with a pharmaceutical composition described herein. The methods can also include administering to a subject in need of therapy an effective amount of a pharmaceutical composition described herein. The composition can include a drug-conjugated lipid or encapsulated drug or drug conjugated to a peptide, wherein the drug is effective for treating the cancer, and wherein the composition may be taken up by cancer cell/tissue, for example, in the subject, and the composition releases the drug to the cancer cells.

The present invention is not limited by the type of cancer expressing Plectin-1 or a fragment or homolog thereof or exhibiting cell surface plectin-1. Indeed, various types of cancer are contemplated for use with the detection methods of the present inventions including, but not limited to lung cancer, bladder cancer, head and/or neck cancer, breast cancer, esophageal cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, stomach cancer, prostate cancer, testicular cancer, ovarian cancer; cervical cancer, endometrial cancer, uterine cancer, pancreatic cancer, colon cancer, colorectal, gastric cancer, kidney cancer, bladder cancer, lymphoma cancer, spleen cancer, thymus cancer, thyroid cancer, brain cancer, neuronal cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, white blood cell cancer (e.g., lymphoma, leukemia, etc.), hereditary non-polyposis cancer (HNPC), colitis-associated cancer, etc. Cancers are further exemplified by sarcomas (such as osteosarcoma and Kaposi's sarcoma).

A "subject" of analysis, diagnosis, or treatment is an animal. Such animals include mammals, preferably a human.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "tumor" refers to an abnormal mass of tissue that results from excessive cell division that is uncontrolled and progressive. It is also called a neoplasm. Tumors may be either benign (not cancerous) or malignant. As used herein, the term "tumor cell", as used herein, refers to any mass of cells that exhibits any uncontrolled growth patterns or altered physiology. Tumor cells may be derived from any tissue within an organism (e.g., a pancreatic ductal tumor cell).

The present invention provides a method of treating a patient with cancer, comprising, a) providing: i) a subject in need of treatment; ii) a pharmaceutical composition comprising a Plectin Targeted Peptide (PTP) conjugated to nanoparticles, such as liposomes carrying a payload, and b) administering the treatment composition to the subject. In some embodiments, the pharmaceutical composition further comprises a therapeutic agent (an example of a payload). In some embodiments, the therapeutic agent is selected from the group consisting of at least one fusion protein, a toxin, and a drug, or a combination thereof.

The following Examples are intended to illustrate the above invention and should not be construed as to narrow its scope. One skilled in the art will readily recognize that the Example suggests many other ways in which the invention could be practiced. It should be understood that numerous variations and modifications may be made while remaining within the scope of the invention.

EXAMPLES

Example 1

Introduction

Advances in cancer medicine lie at the rapidly evolving intersection of -omics technologies. In the clinically emergent field of pharmacogenomics, pharmacology and human genomics are combined to develop new therapies tailored to an individual's unique genetic profile (1). With more expedited human genome sequencing and the genetic profiles of numerous cancer subtypes now defined, the immense potential for pharmacogenetics to improve patient care has been realized, as validated pharmacogenetic markers can streamline clinical management by directing the selection of the most efficacious agent while revealing others that would cause toxicity or would be ineffective.

An exemplary display of this approach has been the identification of molecular alterations in the DNA homologous recombination pathway, including mutations to BRCA1/2, that are utilized to inform caregivers on potential patient response to poly (ADP-ribose) polymerase (PARP) inhibitors.

In companion, oncoproteomics aims to improve clinical management of cancer through identification of unique molecular targets and biomarkers that help diagnose and predict treatment response (2,3). One illustration of this approach is the use of cell surface markers to aid in early cancer diagnosis and facilitate delivery of therapeutic agents preferentially to cancer cells. A pioneering study in this field conducted nearly a decade ago by Kelly et al. utilized phage-based functional proteomics to identify plectin as a new cell surface target in pancreatic ductal adenocarcinoma (PDAC) (4). Subsequent evaluation has revealed plectin exposed on the cell surface in cancers of the ovaries, esophagus, bile duct, and head and neck (5,6). Plectin mislocalized to the cell surface during cancer progression while remaining cytoplasmic in healthy cells. This all or nothing phenotype makes plectin an exquisite target for directed therapies.

Ovarian cancer can serve as a model disease where pharmacogenomics and oncoproteomic technologies can intersect to produce effective anti-cancer therapies. Individuals that harbor mutations in BRCA1/2 proteins that play a role in the repair of double-stranded DNA breaks induced during homologous recombination, have a high risk for breast, pancreas or ovarian cancers (7,8). Ovarian cancer is commonly associated with homologous recombination (HR) deficiency resulting from BRCA1/2 (10-20% of high grade ovarian cancers) and BRCA-like mutations (50% of high grade ovarian cancers) (9-11) which make them sensitive to agents such as PARP inhibitors that prevent DNA repair (12). The US Food and Drug Administration (FDA) recently approved the use of PARP inhibitors (Olaparib, Niraparib and Rucaparib) in the population with BRCA1/2 mutations for treatment of ovarian cancer patients with platinum-sensitivity and recurrent ovarian cancer (13-15). However, 10% of the patients showed adverse side effects, such as the life-threatening conditions of neutropenia and thrombocytopenia, when given the doses necessary to achieve PARP inhibition (12,16-19). About 2% of patients who received Olaparib developed myelodysplastic syndrome and acute myeloid leukemia resulting from excessive PARP inhibition in the bone marrow (20), indicating that off-target effects were substantial in these patients. These studies suggest that the intended goals of PARP inhibition at the tumor site without compromise to patient safety may be achieved by the targeted deposition of an increased drug payload.

One potential route to address this is through a liposomal drug delivery platform. Liposomes have been shown to increase the pharmacokinetic (PK) and pharmacodynamic (PD) profiles of small molecule drugs (21,22), and a number of non-targeted liposomal formulations have already been approved by the FDA in the treatment of cancer (23,24). Similar non-targeted nanoparticle formulations of PARP inhibitors have shown promising results with minimal toxicities in animal studies (25,26). The addition of a target-specific ligand (e.g., peptides or antibodies with affinity for cell surface targets/receptors) to liposomal formulations can amplify the therapeutic index of drugs approved for clinical use (27-30). Peptides offer an appealing starting point for generating target specific liposomes due to the fact that their specificities translate into excellent safety and efficacy profiles in humans. Additionally, peptides are typically known to be less immunogenic and associate with lower production complexity compared to antibodies (31,32).

In previous studies, the cancer-specific phenotype of cell-surface plectin was used to successfully image pancreatic cancer using Plectin Targeted Peptide (PTP) conjugated to nanoparticles or displayed on capsid protein of Adeno Associated Virus (AAV) particles (33). Provided herein is the demonstration that a PARP inhibitor (AZ7379) encapsulated by a PTP conjugated-liposome resulted in a more effective treatment of cancers with BRCA1/2 mutations. The results demonstrate the robust loading of AZ7379 into liposomes and that AZ7379 delivered by PTP targeted liposomes not only enhanced PARP inhibition but also resulted in decelerated tumor growth in animals bearing OVCAR8 (high grade epithelial ovarian cancer (EOC)) tumors. Treatment of mice bearing subcutaneous or intraperitoneal OVCAR8 tumor with PTP liposomes resulted in a 3- and 1.7-fold decrease in tumor volumes, respectively, compared to systemic drug treatment.

MATERIALS AND METHODS

Experimental Materials

Lipids for Liposome Preparation 1,2-dioleoyl-sn-glycerol-3-phosphocholine (DOPC), cholesterol, 1,2-distearoyl-sn-glycero-3-phosphoethanolamine-N-[methoxy(polyethylene glycol)-2000 (DSPE-PEG2000) and DSPE-PEG3400-Maleimide were purchased from Avanti polar lipids, Miami, FL 1,1'-dioctadecyl-3,3,3'3'-tetramethylindotricarbocyanine iodide (DiR) was purchased from Invitrogen, Carlsbad, CA Peptides were synthesized by the Tufts University peptide synthesis core facility using standard FMOC chemistry and Rink-Amide resin (Tufts University, Boston, MA).

Immunofluorescence of Ovarian Cancer Cells and Tumors

Healthy fallopian tube cells, FT132 and ovarian cancer cell lines and tumors (SKOV3 and OVCAR8) were stained for plectin using rabbit monoclonal anti plectin antibody (Abcam, Cambridge, MA) for both IHC and immunofluorescence. PARP activity in OVCAR8 tumors was determined through immunofluorescence of poly ADP ribose (PAR) using anti-PAR rabbit polyclonal (Trevigen, Gaithersburg, MD). Anti y-H2AX (Abcam, Cambridge, MA) was used to quantify double stranded DNA (ds-DNA) breaks after treatment with AZ7379. Anti-LAMP-1 and EEA1 (Abcam, Cambridge, MA) were used to detect early and late endosomes. PARP-1 trapping on chromatin in response to AZ7379 was assessed by Western blotting for PARP-1 (Abcam, Cambridge, MA) in whole cell lysates and chromatin fraction. Appropriate secondary antibodies were employed as needed to identify the primary antibodies: goat anti-rabbit Alexa Fluor 488 (1:250) (Abcam, Cambridge, MA), donkey anti-rabbit Alexa fluor 594 (1:200) (Life Technologies, Frederick, MD).

EXPERIMENTAL METHODS

Immunohistochemistry for Plectin

Paraffin-embedded tumor micro array (TMA) slide was deparaffinized, hydrated with TBS and blocked with H2O2. Antigen retrieval was performed by boiling the slide in Antigen retrieval solution (R&D Systems, Inc. Minneapolis, MN). The slide was later blocked with avidin/biotin (Vector laboratories, Burlingame, CA) and 5% goat serum in TBS followed by incubation overnight at 4° C. with 1:250 dilution of Plectin antibody (Abcam, Cambridge, MA). The slide was washed three times in TBST, followed by incubation with HRP-conjugated goat anti-rabbit secondary antibody (BD Biosciences, San Jose, CA). The slide was developed using DAB and visualized using a microscope. TMA consisted of 20 samples each of 5 high-grade tumor types (endometrioid, mucinous, serous papillary, clear cell, poorly differentiated) and 2 low-grade tumor types (serous cystadenoma and mucinous cystadenoma). Each tumor sample in the TMA was examined by a pathologist (A. M) who assigned a score of 0 (negative), 1+ (weak), 2+ (moderate), and 3+ (strong). The pathologist also determined the percentage of plectin expression and its localization either in the cytosol or in the cell membrane.

Immunofluorescence and Western Blot for Cell Surface Plectin

FT 132, healthy fallopian tube cells were cultured in DMEM supplemented with 10% FBS and ovarian cancer cell lines SKOV3 and OVCAR8 cells were grown either RPMI supplemented with 10% FBS. For plectin immunofluorescence, cells were grown in glass chamber slides. Immunofluorescence was carried out after fixing the cells in 4% paraformaldehyde for 20 min at room temperature followed by blocking the slides with 0.5% BSA in PBS for 1 h at room temperature. Slides were later incubated with primary antibody (anti-plectin rabbit monoclonal antibody) overnight at 4° C. Next day, the slides were washed 3-4 times with PBS and incubated with goat anti-rabbit alexa fluor 488 conjugated antibody for 30 min at room temperature. The slides were later washed 3 times with PBS and mounting media added and cover slip placed over the slide and imaged using confocal microscope (Nikon Eclipse TE2000-E2, Nikon, Melville, NY, USA). Cell surface plectin was quantified after isolating cell surface proteins using cell surface biotinylation protein isolation kit (Thermo Fisher, Waltham, MA). Biotinylated cell surface proteins were isolated according the manufacturer's protocol using streptavidin beads. Plectin was quantified from total cell surface biotinylated proteins of FT 132, SKOV3 and OVCAR cells (~250 k cells) and normalized to the expression levels of cell membrane protein, alpha 1 sodium potassium ATPase (ATP1A1) via Western blot. The relative densities were analyzed by one-way ANOVA followed by Tukey's multiple comparison test to determine if p values were significant ($p<0.05$).

Biolayer Interferometry (BLI) to Study PTP-Liposomes Binding to C-Terminus Fragment of Plectin Biolayer interferometry (BLI) was performed using ForteBio octect Red 96 system (ForteBio, Menlo Park, CA), we used recombinant C-terminus fragment of plectin (4379-4684 aa). All BLI assays were performed in black 96 well plates (Nunc F96 Micro Well plates, Thermo Fisher, Waltham, MA). The total working volume for samples or buffer was 0.2 mL per well and the rpm setting for each equilibration and loading steps was set at 1000 rpm. The association and dissociation step with C-terminus fragment of plectin and peptide-liposomes was carried out at 600 rpm. Prior to each assay, anti-his biosensor tips were pre-wetted in 0.2 mL PBS for at least 10 min followed by equilibrium with PBS for 100 seconds. Anti-his biosensors were then non-covalently loaded with his-tagged C-terminus fragment (50-200 g/mL) (100 sec). Subsequently, association with No peptide, NCP (Negative Control Peptide) and PTP liposomes (40 mM) (300 sec) was be carried out. Finally, the dissociation was monitored in PBS for 600 sec.

Preparation and Characterization of Liposomes

Peptides (7-mers) (PTP—Plectin Targeting Peptide, NCP—Negative Control Peptide) were chemically synthesized with the following modifications on the C-terminus: 7-mer-GGSK(FAM)C.
Peptides were conjugated to DSPE-PEG3400-Maleimide as described previously [37]. Liposomes were prepared by hydration of lipid film prepared with 1,2-dioleoyl-sn-glycerol-3-phosphocholine (Avanti Polar Lipids, Miami, FL) (DOPC): cholesterol: 1,2-distearoyl-sn-glycero-3-phosphoethanolamine-N-[methoxy (polyethylene glycol)-2000 (DSPE-PEG2000): DiR: DSPE-PEG3400-peptide at 46:46:6:1:1 molar ratio (9.5, 4.5, 4.5, 1, and 0.5 mg, respectively). 1,1'-dioctadecyl-3,3,3'3'-tetramethylindotricarbocyanine iodide (DiR, Invitrogen, Carlsbad, CA) was incorporated into the lipid bilayer as a non-exchangeable fluorescent lipid dye that provided for FMT imaging of the peptide-conjugated liposomes in post-MI mice. The lipid mixture was dissolved in 1 ml of chloroform, dried using a rotary evaporator and left in a vacuum desiccator overnight to completely remove residual chloroform. Next day, the lipid film was hydrated with 1 ml of saline and the resulting lipid solution was extruded 41 times using a syringe extruder containing a 0.2 Nuclepore filter (Thermo Fisher Scientific Inc, Waltham, MA). The resulting liposomes were characterized by NanoSight NS300 (Malvern Instruments Ltd, Worcestershire, UK) to determine particle size and concentration. The absorbance of FAM on the peptides enabled the determination of the number of peptides that were incorporated in each liposomal formulation.

Liposomal Binding to Ovarian Cancer Cells

FT 132, SKOV3 and OVCAR8 cells were plated in triplicate in a 96 well black plate at a concentration of 5000 cells per well. After 48 h, liposomes at concentrations ranging from 0.1 to 8 μm were incubated with the three cell lines after washing the wells with PBS buffer for 1 h at 37° C. The cells were later washed with PBS and liposomal DiR intensity was measured using a fluorescent plate reader (FLUOstar omega, BMG Labtech Inc. Cary, NC). PTP liposomal binding to the three cell lines was compared with liposomes containing no peptide (background binding) and with NCP (non-specific binding). Background binding by the no peptide liposomes was subtracted from both the non-specific (NCP) and PTP liposomes. To obtain specific binding of PTP liposomes, we subtracted non-specific (NCP) binding from the total binding by the PTP liposomes.

PK of Peptide Conjugated Liposomes

Each of the peptide-conjugated liposomes was later injected via tail vein in post-MI mice to determine their pharmacokinetics using Fluorescence Molecular Tomography (FMT) imaging. Animals (n=8) were injected with 2 mg of lipid (100 μl containing $1\times10^{11}$ liposomes—No Peptide, NCP and PTP) and DiR present in tumor ROI was imaged using the 750 nm laser of the FMT 4000 system (PerkinElmer, Waltham, MA). The amount of DiR in the tumor region was plotted against time to determine tumor specificity and accumulation of PTP liposomes. Following 24 h post injection, ex vivo imaging of organs was carried out to determine the amount of DiR present in these organs and was represented as percentage of injected dose (% ID). From the same data, Area Under the Curve (AUC) was determined using MATLAB based two-compartment model fit (supplementary file). The presence of DiR in the lipid bilayer of liposomes quickly enabled us to identify the presence of liposomes in the tumor sections. The PK curves were analyzed by one-way ANOVA followed by Tukey's multiple comparison test to determine if p values were significant ($p<0.05$).

In Vitro Growth Inhibition Studies

SKOV3 and OVCAR8 cells were plated in triplicate in a 2 96 well opaque plates at a concentration of 5000 cells per well. After 24 h, cell culture media was replaced with either with fresh media for untreated control wells and others with varying concentration of AZ7379 in RPMI. After 48 h of incubation with AZ7379, the number of viable cells was determined by quantifying ATP using CellTiter-Glo® (Promega, Madison, WI) cell viability luminescent assay kit. 100 µL of CellTiter Glo® reagent was prepared as described by the manual and added to each plate. The plates were incubated for 10 min in the dark followed by measuring luminescence using a FLUOstar OPTIMA microplate reader. Relative growth was calculated with untreated wells as being at 100% and plotted against concentration of AZ7379. Using prism software, IC50 values were determined for OVCAR8 and SKOV3 cells.

Remote Loading of AZ7379

Figure 7A:
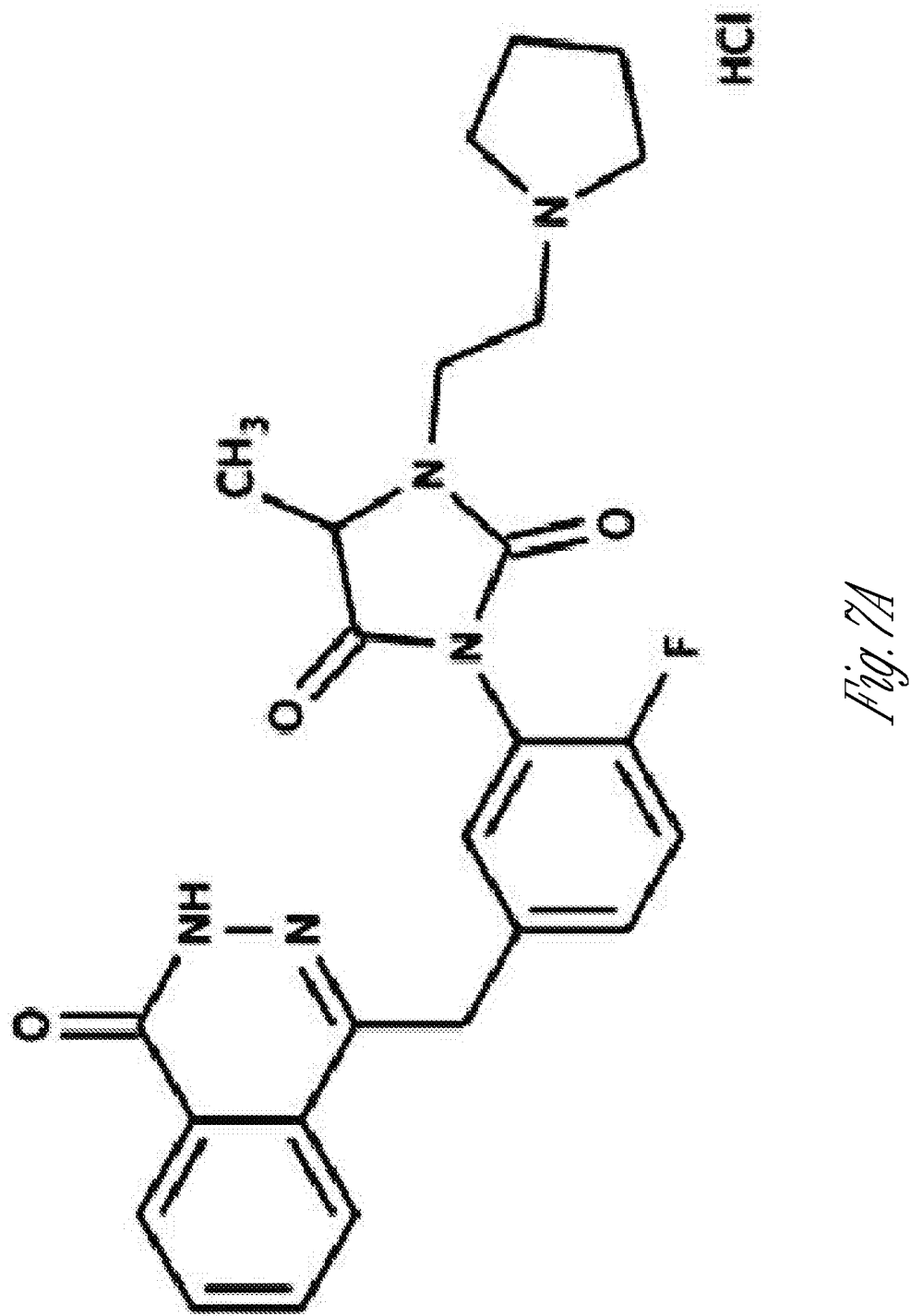
FIG. 7A-C. Physicochemical properties of AZ7379 and in vitro inhibition of PARP-1. A) Structure of AZ7379 B) Physical and Chemical properties of AZ7379. C) In vitro growth inhibition assay in SKOV3 and OVCAR8 cells.

Chemical structure and physiochemical properties of AZ7379 (provided by AstraZeneca) are represented in FIG. 7. Optimization of remote loading was carried out through a two-step process that involved first the identification of buffer exchange method with least loss of lipid followed by determination of the remote loading conditions with high loading efficiencies. These optimization steps were initially carried out with no peptide liposomes followed by PTP liposomes.

For remote loading of AZ7379, liposomes were prepared as described previously by reverse phase evaporation (37). In brief, the lipid mixture containing DOPC, cholesterol, DSPE-PEG(2k) were dissolved in 1 mL of chloroform and to this 3 mL of ethyl ether and 1 mL of 0.25 M ammonium sulfate solution was added. This lipid mixture was sonicated with a probe sonicator (XL2020, Misonix Inc, Farmingdale, NY) to prepare water-in-oil emulsion, and with a help of a rotary evaporator, organic solvents were removed under vacuum. Liposomes were prepared by passing through a 0.2 µm Nuclepore filter using a syringe extruder. Before remote loading, the ammonium sulfate present outside of the liposomes was removed by passing twice through size-exclusion, Zeba Spin desalting columns (Thermo Scientific, Rockford, IL). Zeba spin columns were washed three times with 10 mM HEPES buffer (pH 7.4) by spinning columns in a swinging bucket rotor at 1500×g for 1 min before loading ammonium sulfate liposomes. One-half mg of AZ7379 (2.5 mg/mL in 10 mM HEPES pH 7.4) was then incubated with 5 mg of lipid (20 mg/mL) at 65° C. for 1 h or 4 h and at room temperature for 4 h. The free drug was removed by passing through Zeba spin columns that were washed with 10 mM HEPES buffer, and the drug to lipid ratio for the purified liposomes was determined by HPLC using a combination of spectrophotometric and evaporative light scattering detectors as described previously (37).

AZ7379 Release Kinetics

The efficiency of remote loading was typically 100-120 µg of AZ7379 per mg of lipid for No Pep liposomes and 80 µg of AZ7379 per mg of lipid for PTP and NCP liposomes quantified by HPLC methods. The size and concentration of the liposomes was determined using NanoSight. AZ7379-loaded No Pep and PTP liposomes were mixed with 50% fetal bovine serum in saline and the release was assessed at regular time points by measuring the amount of drug released into 50% FBS maintained at 37° C. by HPLC. Release rates were plotted for each of the liposomal formulations as cumulative % release over time.

In Vivo Anti-Tumor Effects of AZ7379

Figure 5A:
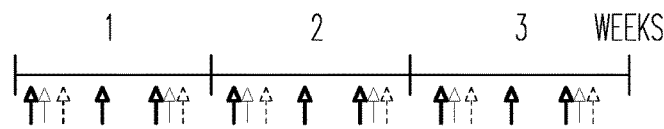
FIGS. 5A-C. PARP inhibition in OVCAR8 tumors following AZ7379 delivery. A) Experimental design for measuring PD following AZ7379 delivery. There were 7 groups—1. Untreated (n=5), 2. Systemic AZ7379-1 (n=5), 3. Systemic AZ7379-2 (n=5), 4. No Peptide liposomes AZ7379 (No Pep AZ7379) (n=6), 5. NCP liposomes AZ7379 (n=6), 6. PTP liposomes AZ7379-2 (n=5), 7. PTP liposomes AZ7379-2 (n=6). Systemic AZ7379 was delivered three times a week by oral gavage and liposomal groups were delivered twice a week via tail vein injections. B) Tumor volume (mm3) was measured every week following treatment and plotted over time to determine the efficacy of each treatment group. PTP liposomes loaded with AZ7379 were effective in preventing tumor growth compared to other groups. C) Final tumor volume from all the 7 groups indicates significantly lower tumor volumes with PTP liposomes-1,-2 ($p<0.05$). Tumor volume was not significant between untreated and systemic-1 and -2.

Animal experiments were performed after approval from the Institutional Animal Care and Use Committee (IACUC), University of Virginia. To determine the benefits of plectin-specific delivery over systemic delivery, tumor volume over time and extent of PAR formation at the end of treatment period was compared after treating mice bearing OVCAR8 tumors (2 tumors per animal) with PTP liposomes loaded with AZ7379 vs. systemic AZ7379. Athymic nude mice (n=28) were injected subcutaneously in two regions with OVCAR8 cells and once the tumors reached a volume of ~100 mm$^3$, mice were randomly assigned to one of 5 different groups: 1) Untreated (n=5), 2) Systemic AZ7379-0.5 (n=5), 3) Systemic AZ7379-1 (n=6) 4) No Pep AZ7379 (n=6), 5) Negative Control Peptide (NCP) AZ7379 (n=6), 6) PTP AZ7379-0.5 (n=6), and 7) PTP AZ7379-1 (n=6). Systemic AZ7379-0.5 and -1 were given via oral gavage 3 times a week at 0.5 and 1 µmol/Kg/gavage respectively and liposomes were injected via tail vein 2 times a week at 1.5 µmol/Kg/injection except PTP AZ7379-0.5, where liposomes were injected twice a week at 0.75 µmol/Kg/injection (FIG. 5A). Tumor volume was measured using calipers and average tumor volume per group was plotted against time. Tumor volume was determined every week and calculated using this formula TV= ((1×w×w)/2). Mouse body weight was also recorded every week to check if there were any sudden changes in the body weight due to the tumors. Tumor volumes from each group were analyzed by paired t test to determine if the treatment groups were significant (P<0.05). After 3 weeks of treatment, mice were euthanized and one tumor from each animal was snap frozen and used for Western blot for PAR and another tumor was fixed in 4% paraformaldehyde to quantify PAR through immunofluorescence.

A second ovarian cancer model was employed to mimic metastasis to the intraperitoneal (IP) cavity and to evaluate liver function and myeloid cell population in response to AZ7379 treatment. OVCAR8 cells expressing iRFP720 protein were injected intraperitoneally, and after 7 days the mice were imaged via FMT and randomized into treatment groups; 1) Untreated (n=6), 2) Systemic AZ7379 (n=6), 3) No Pep AZ7379 (n=6), and 4) PTP AZ7379 (n=6). Systemic AZ7379 was delivered via oral gavage 3 times a week at 1 µmol/Kg/gavage and liposomes were injected via tail vein 2 times a week at 1.5 µmol/Kg/injection. Mice were treated for 3 weeks with similar dosing described previously in the subcutaneous model. Tumor growth was monitored by performing FMT imaging of mice twice a week. At the end of 3 weeks, blood granulocyte and monocyte populations were quantified by flow cytometry. Liver function was determined by measuring aspartate aminotransferase (AST) and alanine aminotransferase (ALT) (Sigma-Aldrich, St. Louis, MO) levels in the serum. After necroscopy, visible tumor nodules were counted and the organs in the IP cavity were imaged ex vivo via FMT. The fluorescence from each organ was normalized to its weight. PAR levels in the tumors were determined by immunoblot.

PAR Quantification (Immunofluorescence and Western Blot)

The tumor samples were fixed in 4% paraformaldehyde and frozen in OCT so that 5 µm sections could be prepared using a cryostat. PARP-1 activity was assessed by quantitative image analysis as the percentage of poly (ADP-ribose) (PAR) positive nuclei present in tumor sections. PAR accumulation was assessed in at least 5, 5 µm sections taken from each tumor using antibody recognizing PAR (Trevigen, Gaitherburg, MD). In the image analysis, a total of 5, 20× and 5, 60× images from each tumor was used for PAR quantification. Percent PAR+ area within each tumor section was determined using imageJ and was compared between the different groups. The second tumor from each animal was lysed and used for PAR quantification using Western blot analysis using the same antibody as described above. 10 µg of protein from 3 animals from each group were separated on a SDS gel followed by transferring of proteins on to nitrocellulose membrane. Once the proteins were transferred, the membrane was blocked using 5% non-fat dry milk in Tris buffered Saline (TBS) buffer containing 0.2% tweem-20 (TBST) for 30 min at room temperature on a shaker. The membrane was later incubated with anti-PAR rabbit polyclonal antibody at 1:1000 dilution in 5% milk in TBST overnight at 4° C. Next day, the membrane was washed 4 times with TBST followed by incubation with donkey anti-rabbit HRP antibody (GE healthcare biosciences, Pittsburg, PA) at 1:10000 dilution in 5% milk in TBST for 20 min at room temperature. The membrane was washed 3 times with TBST followed by incubation with Immobilon Western chemiluminescent HRP substrate (Emdmillipore, Billerica, MA) for 2 min at room temperature. The membrane was later exposed to autoradiography film in a dark room and developed using an x-ray film developer. After the film development, membrane is washed with TBST overnight at 4° C. The membrane was later blotted for alpha-actin by incubating overnight at 1:5000 dilution in 5% milk in TBST at 4° C. Next day, the membrane was washed and incubated with goat anti-mouse HRP antibody and actin bands imaged as described above. PAR and actin bands on x-ray film were quantified using densitometer (Bio-Rad GS-800, Bio-Rad, Hercules, CA) and ImageQuant software (GE healthcare biosciences, Pittsburg, PA). PAR to actin density for each tumor sample was plotted for each experimental group. Ratios of PAR to actin were analyzed by one-way ANOVA followed by Tukey's multiple comparison test to determine if p values were significant (p<0.05).

Flow Cytometry 500-700 µL of blood was drawn from each mouse via cardiac puncture and placed in a tube containing 1 mL of 5 mM EDTA/Hank's balanced saline solution (—Mg, —Ca) (HBSS). An additional 10 ml of HBSS was added and the blood was centrifuged, and the cell pellet was resuspended in MACS buffer (0.5% BSA, 250 mM EDTA in PBS). To remove RBCs, the cells were incubated with
ACK lysis buffer (Thermo Scientific, Waltham, MA) for 5 min at room temperature and immediately quenched with complete media. The cells were then washed in MACS buffer and counted using a hemocytometer. For $0.35 \times 10^6$ cells, anti-Ly-6G PE (1:200 dilution) (BioLegend, San Diego, CA), anti-Ly-6C PE/Dazzle (1:800 dilution) (BioLegend, San Diego, CA), anti-CD45 PE/cy5 (1:800 dilution) (BioLegend, San Diego, CA), anti-CD11b PE/cy7 (1:800 dilution) (BioLegend, San Diego, CA), and Live dead stain (1:200) (Thermo Scientific, Waltham, MA) were incubated for 30 min and washed 3 times before fixing the cells in 4% paraformaldehyde. The stained blood cells were analyzed by CyAn ADP (Beckman Coulter, Brea, CA).

Statistical Analysis

All experiments were repeated at least three times, and statistical analysis of the data was performed by one-way analysis of variance (ANOVA) followed by Tukey's multiple comparison test. PK of different liposomes were compared using paired t-test to determine if they were significant. Tumor volumes between groups were compared using paired t-test to determine if they were significant. All data represented here is mean±standard deviation of at least three independent measurements. For all comparisons, p<0.05 was considered significant.

RESULTS

Plectin Expression in Ovarian Cancer

Plectin was previously identified in as a PDAC cell surface biomarker through a phage display based proteomics approach (4-6). In follow-up studies a plectin targeting peptide (PTP) that displayed specific binding to plectin was generated and subsequently utilized in vivo to image animals bearing pancreatic tumors (4,5,33,34). Immunohistochemical analyses of human patient specimens demonstrated high levels of plectin expression cancers of the pancreas, ovaries, head and neck but low or medium levels of expression in healthy specimens. However, in the case of ovarian cancer, only serous carcinoma was evaluated. Therefore, plectin analysis was expanded to tumor microarrays (TMA) from several different classes of low and high-grade ovarian tumors. Each TMA spot was examined by a pathologist (A. M) who assigned both the cellular localization of plectin, cytosol or membrane, and a score for relative expression, with 0 (negative), 1+ (weak), 2+ (moderate), and 3+ (strong) (Table 1). The results indicate that plectin expression was either moderate or strong for all types of ovarian cancer that were evaluated. In serous, clear cell and poorly differentiated ovarian cancer specimens, plectin expression was observed in more than 80% of the cancer cells and its expression was mainly localized to the cell membrane (FIG. 1A). Conversely, plectin was mainly cytosolic in endometrioid and mucinous cancer specimens, as well as in low-grade tumors such as serous cystadenoma and mucinous cystadenoma. These results indicate that plectin localization to the cell membrane occurs in several types of human ovarian cancer—including clear cell carcinoma, which has a paucity of treatment options.

TABLE 1

Plectin expression and cellular localization

| Tumor type | Score | Percentage | Localization |
|---|---|---|---|
| Endometrioid | 2+ | >80 | cytosol |
| Mucinous | 2+ | >80 | cytosol |
| Serous papillary | 3+ | >90 | cell Membrane |
| Clear cell | 3+ | >80 | cell membrane |
| Poorly differentiated | 3+ | >80 | cell membrane |
| Serous cystadenoma | 2+ | >70 | cytosol |
| Mucinous cystadenoma | 2+ | >70 | cytosol |

Figure 1B:
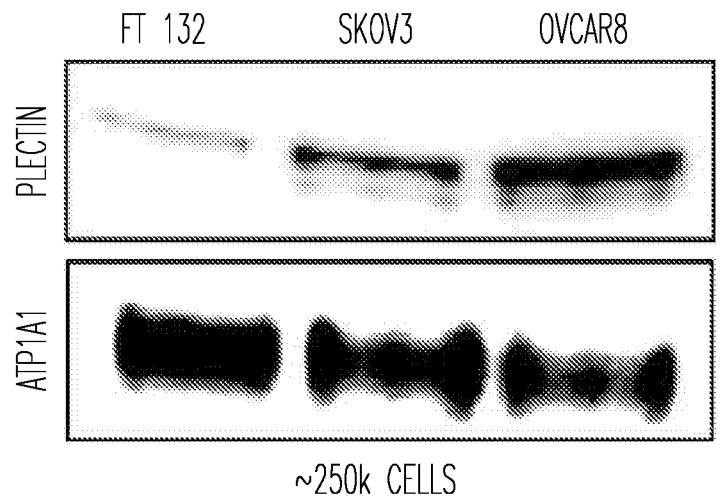
Figure 1C:
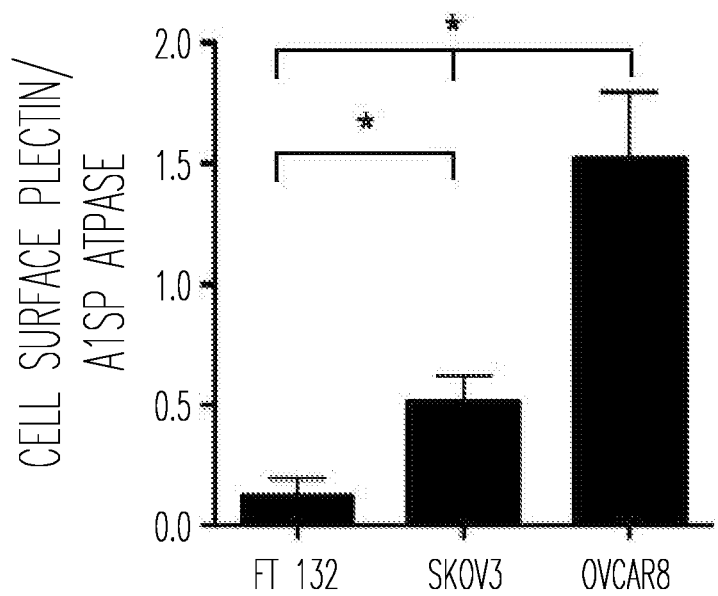

Note:
0 = negative, 1+ weak, 2+ moderate, 3+ strong.
Percentage - Percentage of cells positive To further evaluate plectin cell surface expression, cell surface biotinylation was performed on healthy human fallopian tube epithelial cells (FTECs)-FT132 (35) and two ovarian cancer cell lines of different grade and BRCA1/2 status, SKOV3 (low-grade, WT BRCA1/2) and OVCAR8 (high-grade, mutated BRCA1/2). Immunoblot detection of the surface protein isolates revealed that indeed plectin is present on the cell surface and expressed at the highest levels in high grade OVCAR8 cells (12-fold over FT132). The low grade SKOV3 cells had reduced expression compared to the OVCAR8, however expression was still markedly above that of healthy cells (3-fold over FT132) (FIGS. 1B and C).

Preparation and Characterization of PTP Liposomes

Figure 2A:
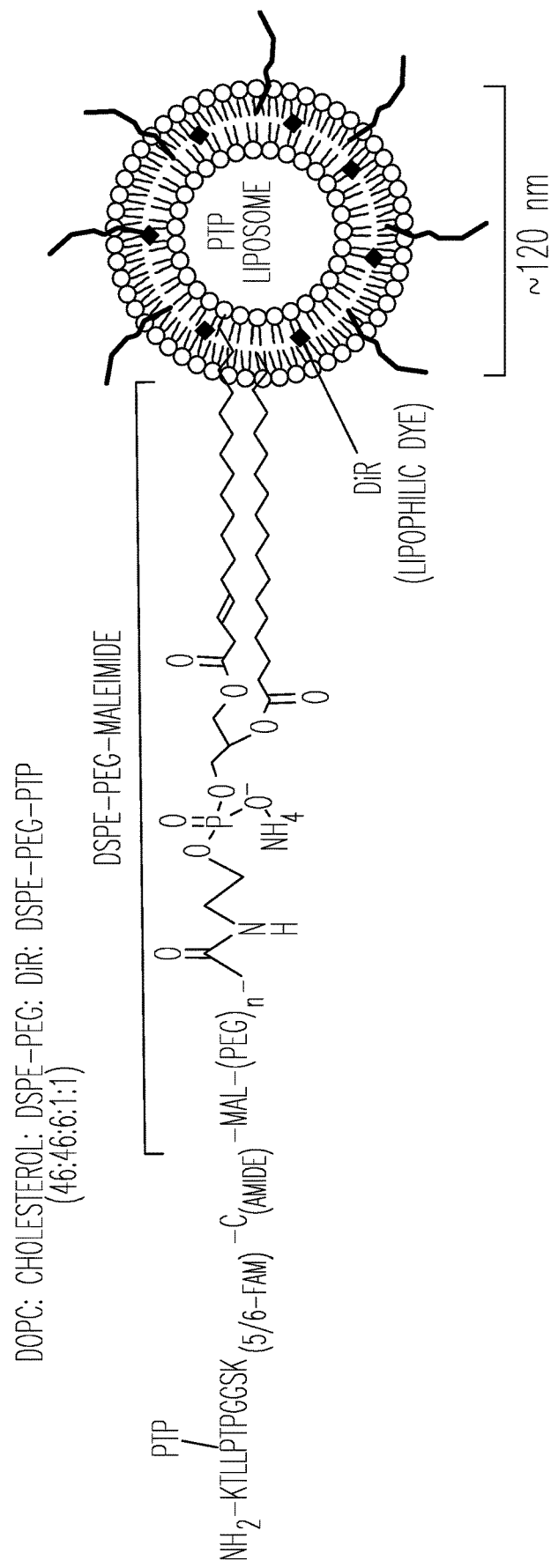
FIGS. 2A-B described plectin-targeted peptide (PTP) liposomes binding to Plectin. A) PTP peptide was conjugated to DSPE-PEG-MALEIMIDE via the thiol present on the C-terminus of the peptide. B) Binding of PTP liposomes to the C-terminus of Plectin was carried out using Biolayer Interferometry (BLI). The anti-His antibody coated sensors were used to bind his-tagged plectin fragment followed by association with no peptide, NCP and PTP liposomes. Association and dissociation response was seen by PTP liposomes but not with No peptide and NCP liposomes. (B-baseline).

Following confirmation of cell surface plectin expression, liposomal preparations were generated and characterized. First, peptide sequences KTLLPTPGGSK(FAM)C (Plectin Targeting Peptide—PTP; SEQ ID NO: 1) and TAL-PRLNGGSK(FAM)C (Negative Control Peptide—NCP; SEQ ID NO: 25) were conjugated to DSPE-PEG3400-Maleimide to form PTP-PEG3400-DSPE (FIG. 2A). No peptide containing liposomes (No peptide or No Pep) were prepared in parallel as an additional control. The size and concentration of the three liposome formulations, as determined by NanoSight analysis, were similar and ranged between 110-120 nm and $3 \times 10^{13} \pm 4 \times 10^{11}$ particles per mL, respectively. Zeta potential for liposomes without peptide was 32±1.2 mV and liposomes with peptides (NCP or PTP) had a zeta potential of 31±1.6 mV, suggesting very little influence of peptide charge on the zeta potential of liposomes.

Figure 2B:
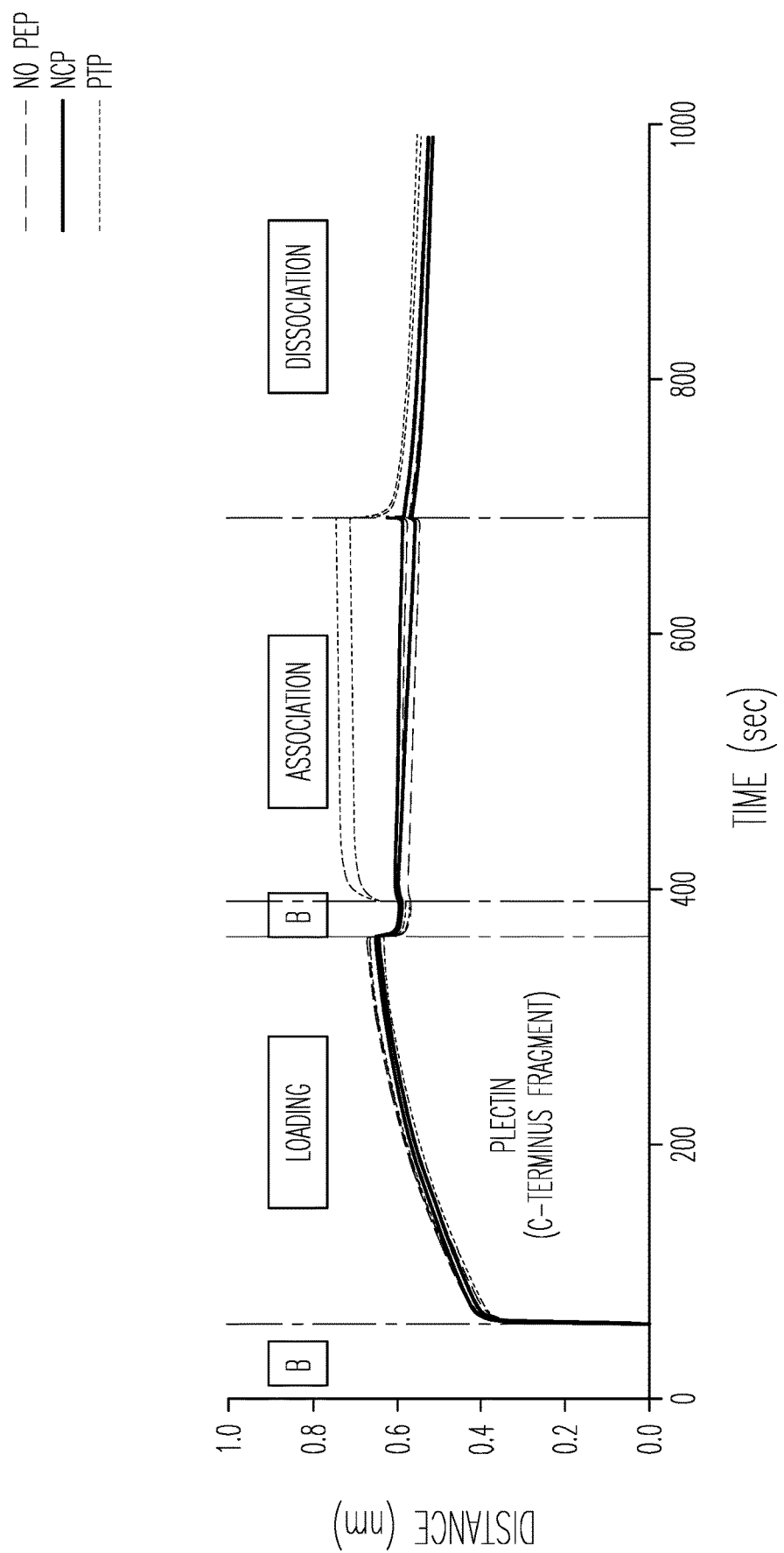
Figure 3A:
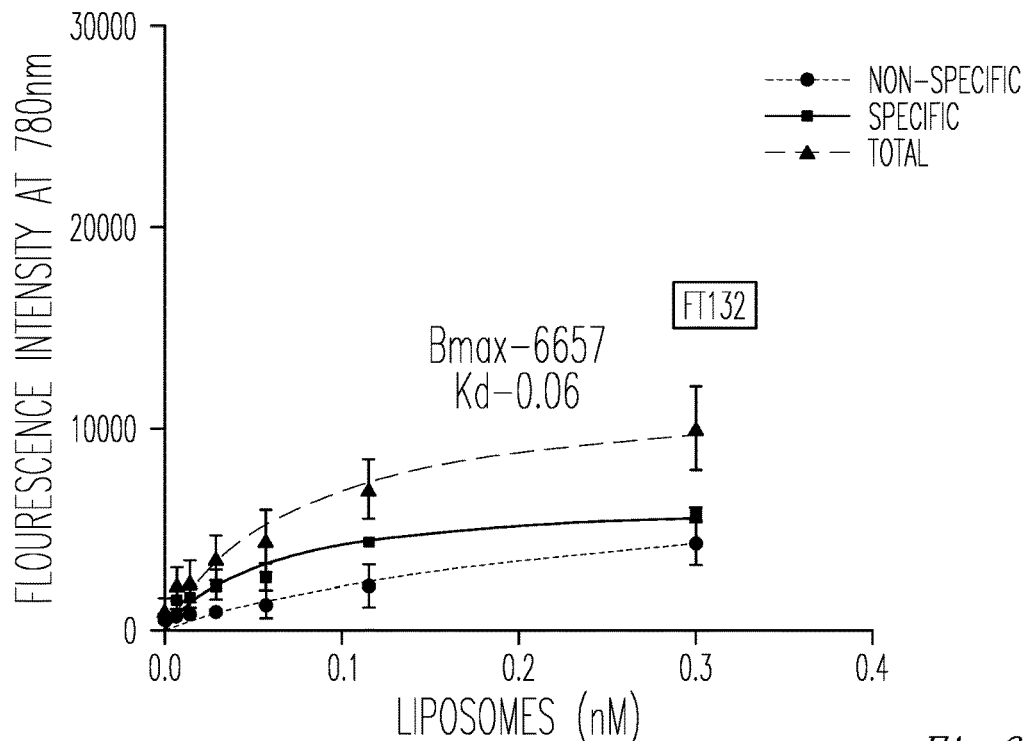
FIGS. 3A-C. PTP liposomes bind to SKOV3 and OVCAR8 cells. Cell binding assay (ELISA) was carried out to assess PTP liposome association to cell surface plectin on SKOV3 and OVCAR8 cells. Liposomes (No Pep, NCP and PTP) at varying concentrations were incubated with FT132, SKOV3 and OVCAR8 cells for 1 h at 37° C. The binding of No Pep liposomes was subtracted from NCP to determine the non-specific binding. NCP binding was subtracted from PTP liposomes to determine specific binding of PTP liposomes to A) FT132, B) SKOV3 and C) OVCAR8 cells for 1 h at 37° C. followed by quantification of DiR using fluorescent plate reader.
Figure 3B:
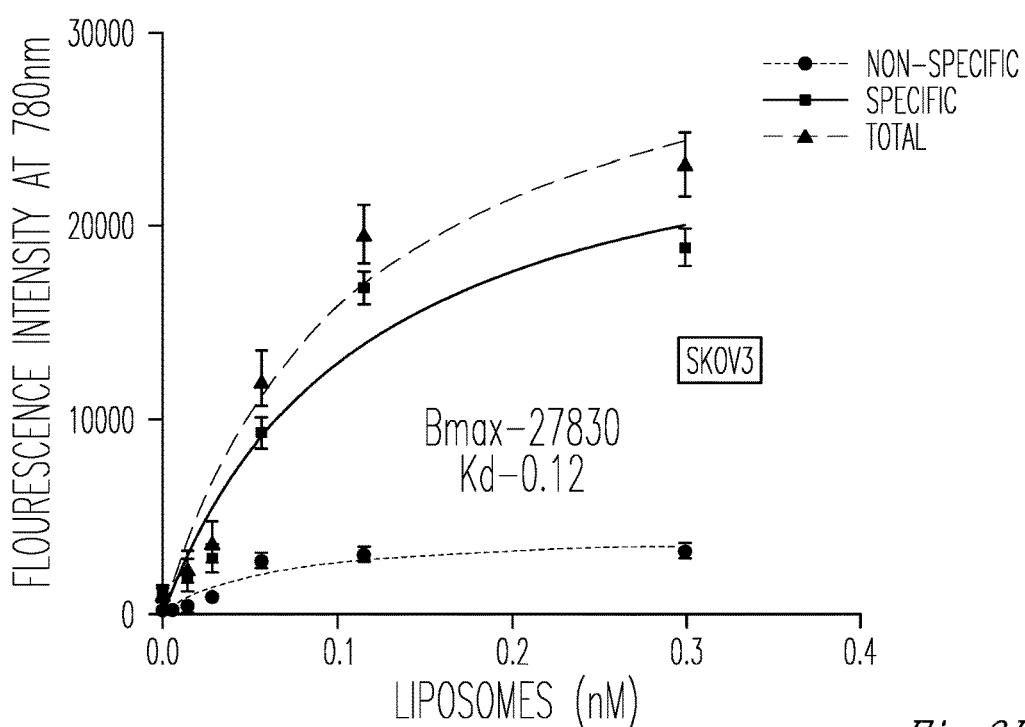
Figure 3C:
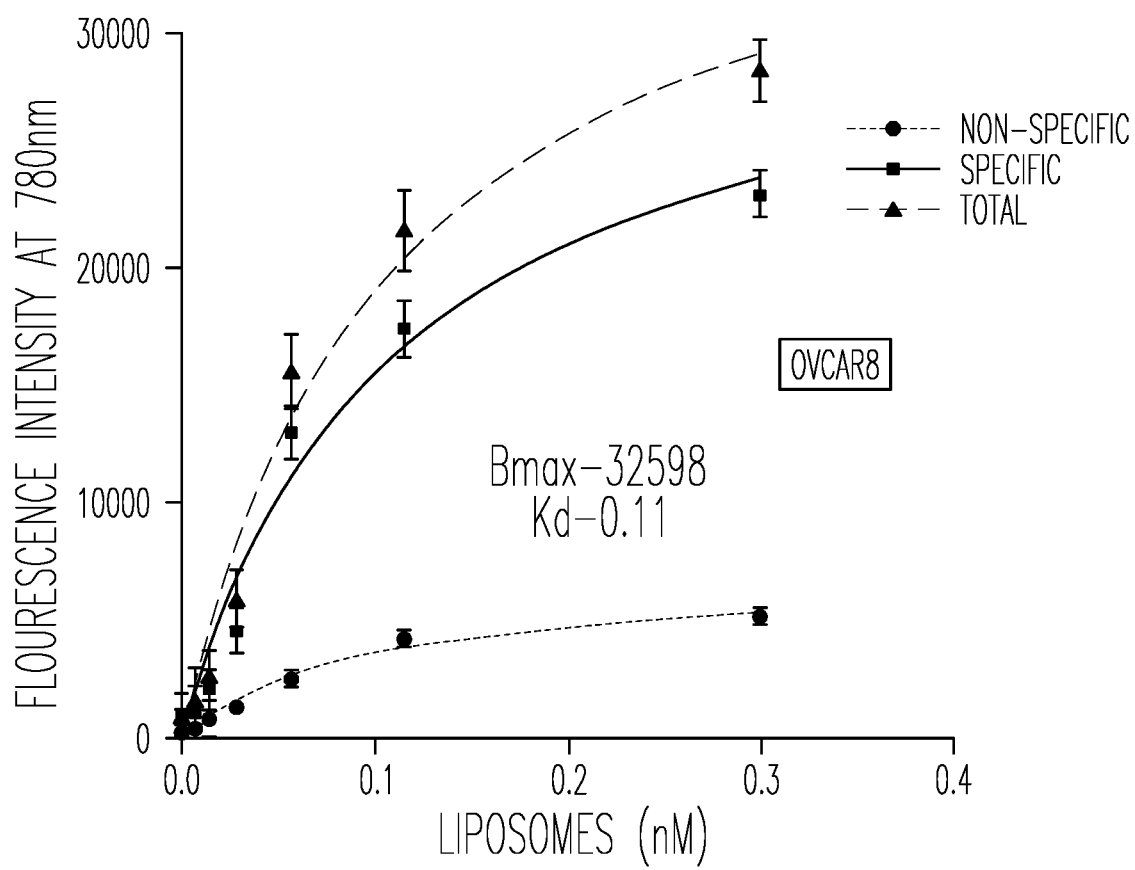

To verify that the PTP liposome formulation maintained its ability to bind to plectin, the ForteBio octet system and Biolayer interferometry (BLI) were used to measure the binding of PTP, NCP, and no peptide liposomes to recombinant c-terminus fragment of plectin (4379-4384 aa) (FIG. 2B). Only PTP liposomes associated with plectin, confirming not only their specificity for plectin but also that the incorporated PTP-DSPE conjugate was in the correct orientation. PTP liposomes display binding specificity and enhanced tumor uptake Based on the expression data presented in FIG. 1B, C, the FT 132, SKOV3 and OVCAR8 cell lines were utilized to determine if the PTP liposomes showed specificity in a cell-based context. Liposomes containing the lipophilic dye DiR were serially diluted and incubated with each of the three cell lines, followed by measurement of fluorescent intensity to quantify liposome-cell binding. PTP liposomes bound to SKOV3 and OVCAR8 cells with a Kd of 0.12 nM and 0.11 nM, respectively (FIG. 3). In contrast, PTP liposomes did not exhibit significant binding above background when incubated with healthy fallopian tube cells, FT132 (FIG. 3A). No peptide and NCP liposomes demonstrated similar background levels of binding to the three cell types. These results indicate that cells with the highest level of cell surface plectin also display the greatest capacity to bind specifically to the PTP liposomes. In addition to binding, it was also determined whether the PTP liposomes were endocytosed. PTP liposomes containing DiR were added to the culture of OVCAR8 cells in which EEA1 (early endosome antigen 1) or LAMP-1 (lysosomal-associated membrane protein 1) (late endosomal biomarker) were co-stained. No Pep and PTP were both endocytosed but at 8 h, PTP liposomes were associated with EEA1 2.3-fold greater compared to No Pep liposomes. Similarly, at 24 h PTP liposomes associated with LAMP-1 1.6-fold greater when compared to No Pep liposomes.

Figure 4A:
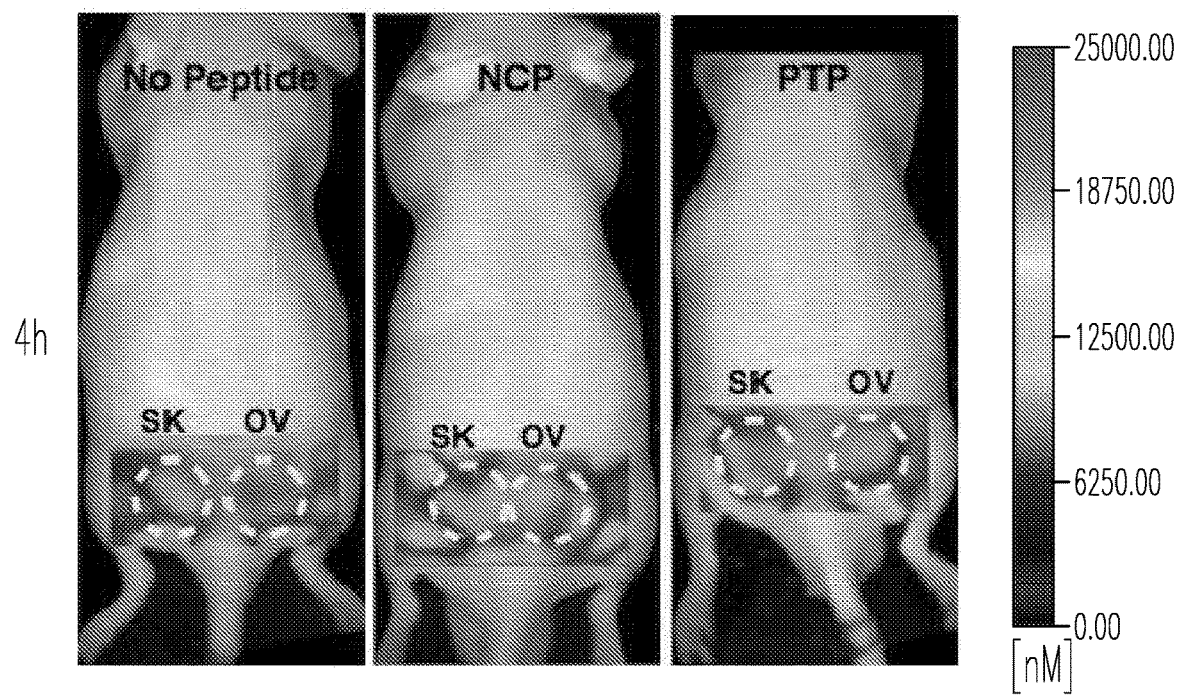
FIGS. 4A-F. PTP liposomes accumulate in OVCAR8 tumors to a greater extent compared to SKOV3. A) In vivo images of mice bearing SKOV3 and OVCAR8 tumors injected with No Peptide (No Pep), Negative Control Peptide (NCP) and PTP liposomes, (t=4 h) B) Same animals were imaged at 24 h post-injection. C) and D) Graphs showing pharmacokinetics (percent injected dose (DiR)) of three liposomes obtained using FMT imaging followed by image analysis using the tumor as the region of interest (ROI) (white dotted circles). FMT imaging of the liposomal preparations was performed in live mice (n=6). Liposomes displaying a NCP were included to compare random vs. targeted liposome kinetics. In this instance, targeted liposome accumulation was largely consistent with the density of available cellular targets. (* represents p<0.05) E) Biodistribution of liposomes 24 h post-injection from different organs including the tumors. (* represents p<0.05) F) Following 24 h of in vivo imaging, tumor sections were prepared and stained for plectin followed by confocal microscopy to look at plectin and DiR colocalization. Confocal images of the tumor sections revealed DiR labeled liposomes (red) accumulated in the plectin+ (green) SKOV3 and OVCAR8 cells. (DAPI-blue) (Scale bar; 20 μm).
Figure 4B:
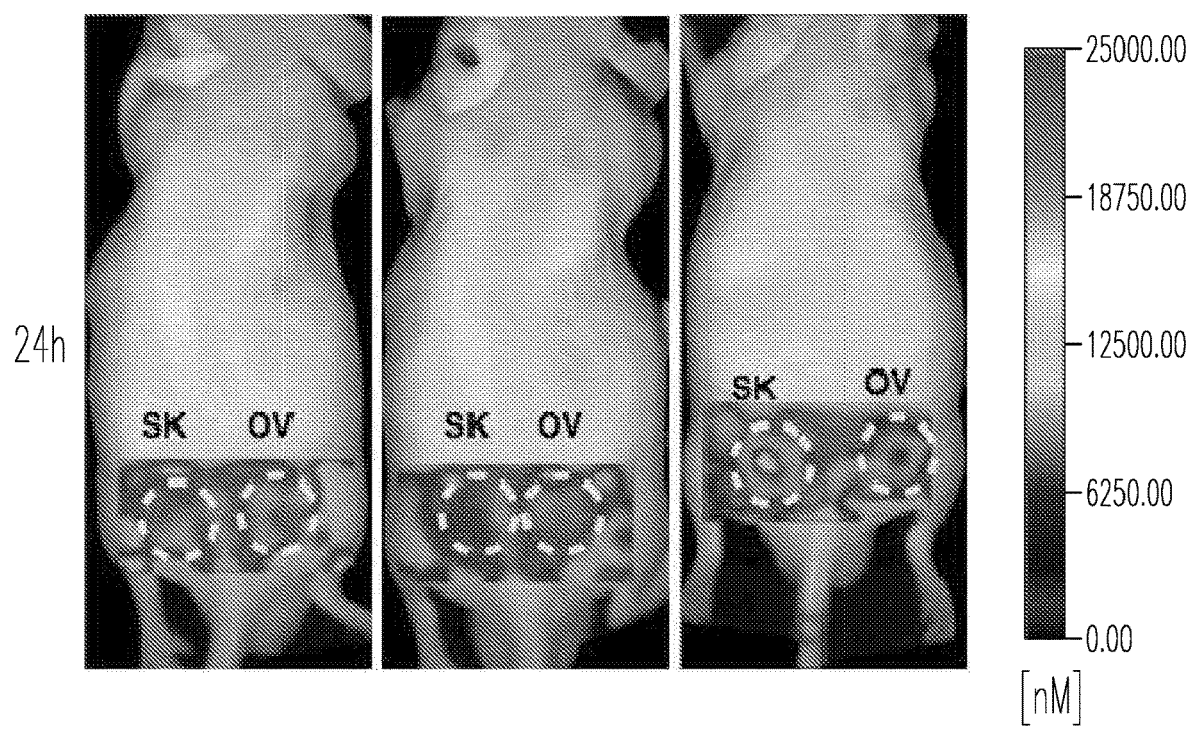
Figure 4C:
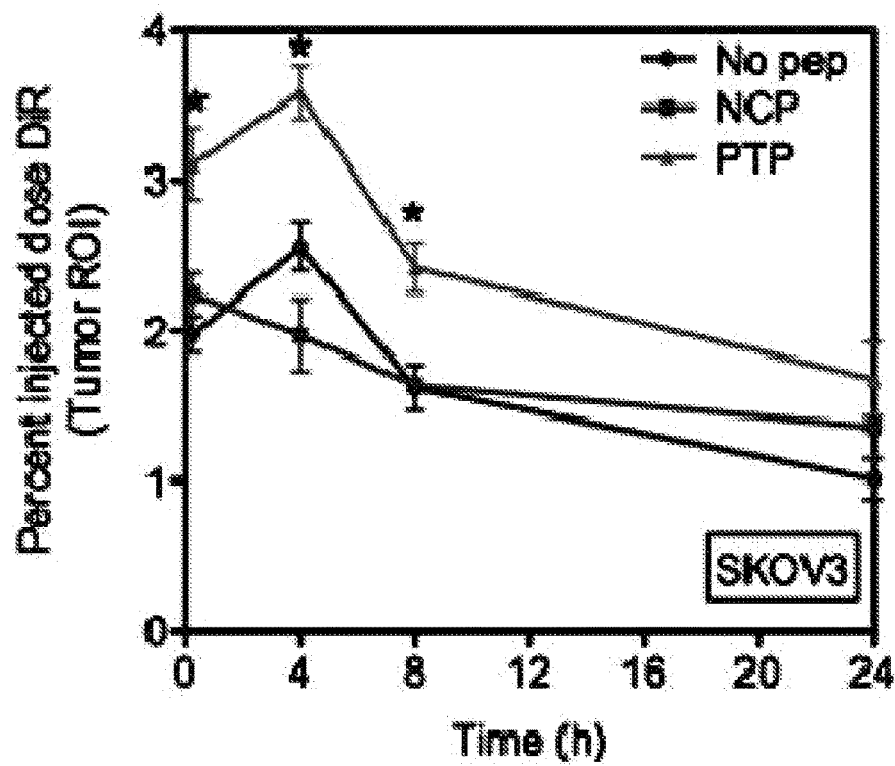
Figure 4D:
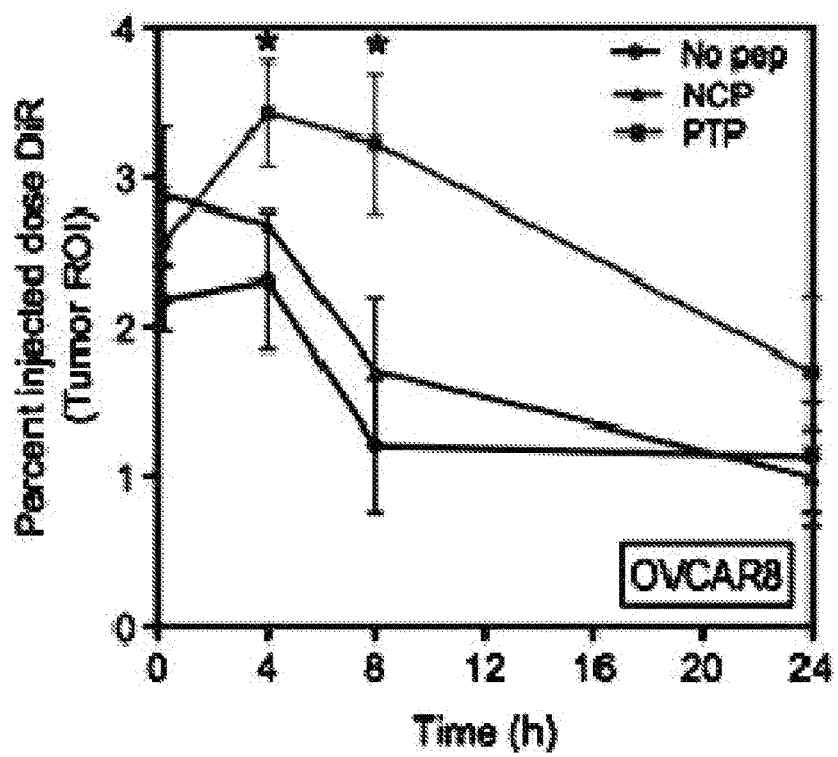
Figure 4E:
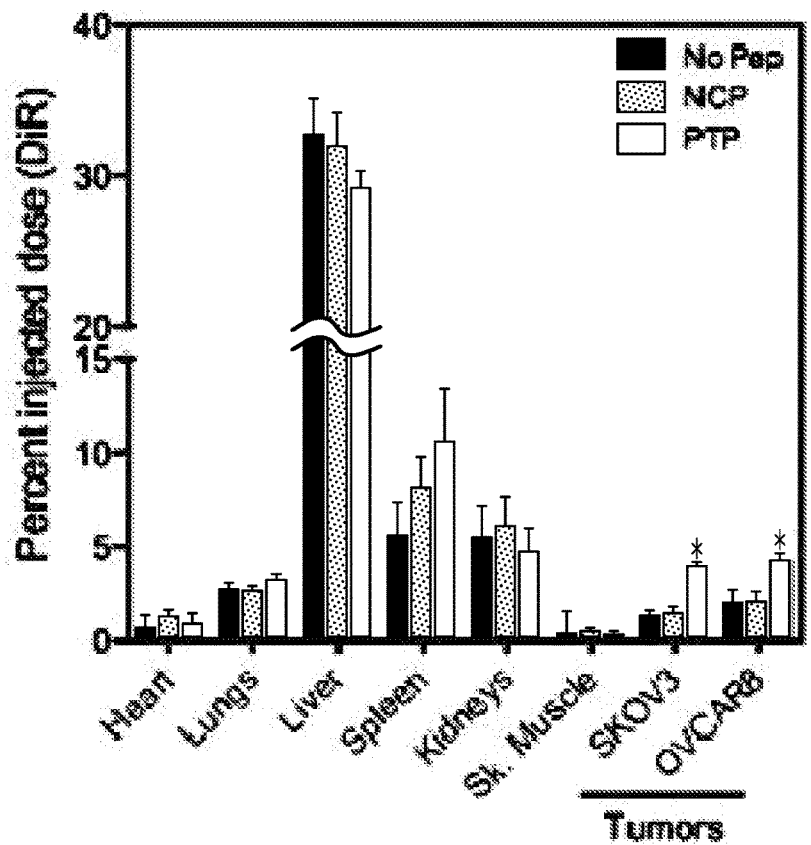

Next, the PK and biodistribution of No peptide, NCP, and PTP liposomes (1 mg of lipid) was studied in SKOV3 and OVCAR8 subcutaneous tumor models using Fluorescence Molecular Tomography (FMT), which due to the presence of DiR (a lipophilic, near-IR dye) in the lipid bilayer of liposomes allowed PK analysis through non-invasive serial imaging (36) (FIGS. 4A & B). The amount of DiR in the tumor region was quantified from the reconstructed images using FMT system software and the percent-injected dose (% ID) of liposomes (DiR) was plotted against time for both SKOV3 and OVCAR8 tumors (FIGS. 4C and D). Using a two-compartment model fit, a 1.3 and 1.9-fold greater area under the curve (AUC) was observed of PTP liposomes in SKOV3 and OVCAR8 tumors, respectively, compared to the No peptide liposomes (AUC 50 (PTP) to 38 (No Pep) SKOV3; AUC 64 (PTP) to 34 (No pep) OVCAR8) or NCP liposomes (AUC 39 SKOV3; AUC 41 OVCAR8). AUC represents the total exposure of the tumor to the liposome with a higher AUC indicating higher drug delivery to the tumor. A direct comparison of PTP liposome in tumor bearing animals (AUC 64 (OVCAR), 50 (SKOV3) and ex vivo biodistribution analysis at 24 h post-injection (4.3 pmoles (OVCAR), 3.8 (SKOV3) indicated ~1.2-fold greater amount of accumulation in OVCAR8 compared to SKOV3 tumors (FIG. 4E). Association of PTP liposomes with OVCAR8 tumors was ~1.3-fold greater than SKOV3 tumors, which was comparable to what we observed in cell binding assays (FIGS. 3 and 4).

Figure 4F:
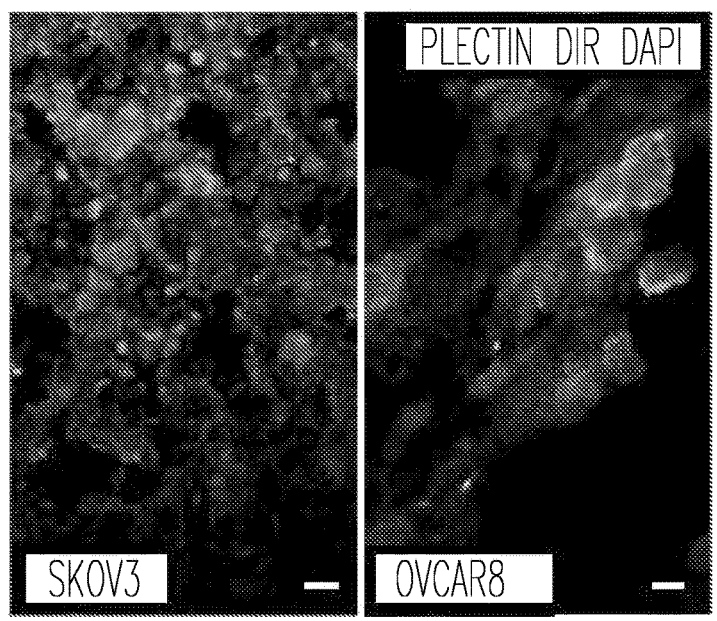

The delivery platform tested here is founded on the targeted delivery of liposomal-encapsulated drug. Therefore, it was confirmed that the results presented above were in fact due to PTP liposomes binding to OVCAR8 and SKOV3 cells and no other cells within the tumor milieu. Specimens from SKOV3 and OVCAR8 tumor-bearing mice were harvested 24 h post-liposomal DiR injection and stained for plectin expression. Immunofluorescence analysis indicated a high degree of overlap of DiR+ liposomes and plectin positive cancer cells, suggesting that liposomes accumulated primarily in the targeted tumor cells (FIG. 4F). When explored further, No Pep liposomes associated with only 20% of plectin+ or CD31+ cells but PTP liposomes associated with 50% of plectin+ cells and 24% fo CD31+ cells suggesting a shift in the distribution of liposomes favoring plectin+ tumor cells.

Remote Loading of AZ7379 into PTP Liposomes and Their Stability in 50% Animal Serum It is well established that cancer cells harboring mutant BRACA1/2 are more susceptible to PARP inhibition than are WT BRAC1/2 cells. For maximum efficacy and minimum off target effects, PARP inhibitors must be delivered specifically to the target cell at high payload. Therefore, the liposome remote loading capacity of several PARP inhibitors, including Olaparib, AZ7379, AZ3598, and AZ9594, was determined. The results indicated that the loading efficiency of Olaparib, AZ3598, and AZ9594 was less than 30% (data not shown), however, AZ7379 displayed a greater than 60% efficiency.

The drug was validated by measuring SKOV3 and OVCAR8 growth at different concentrations of drug. As expected, the BRCA1/2 mutated OVCAR8 were more susceptible to AZ7379-induced growth inhibition than WT BRCA SKOV3, with a demonstrated $IC_{50}=177$ μM AZ7379. The loading, composition, and stability of the liposomal formulations were characterized. To optimize remote loading protocol, the buffer exchange conditions were determined that resulted in the greatest lipid retention during preparation. Size exclusion permitted the greatest recovery of lipid (41% recovered, with identical mole ratios of lipids as in initial lipid mixture), as determined by HPLC, compared to ultracentrifugation (32%) or dialysis (38%). Second, it was determined that a 4-hr. incubation at room temperature was optimal for loading AZ7379 compared to two other tested conditions, which lead to a 70% loading efficiency with a drug (µg) to lipid (mg) ratio of 135±2.3. Nanoparticle tracking analysis indicated that liposome size was consistent at each stage (initial, after buffer exchange (BE), after remote loading (RL)), however the concentration of liposomes decreased progressively, which correlated with the HPLC quantification of final lipid content (~41% lipid recovered). Cryo-TEM also revealed that the structure of liposomes remained intact during this process.

Using the above optimized conditions, similar parameters in remote loading of AZ7379 into PTP liposomes was evaluated. The number of peptides/liposomes at each step was quantified using the fluorescent molecule, FAM, present on the C terminal end of the PTP and observed about 10% loss of PTP-DSPE conjugate, indicating that it was incorporated stably. The size of PTP liposomes (~110 nm) was not altered and the loss of lipid was comparable to No Pep liposomes (data not shown). While the final drug (µg) to lipid (mg) ratio was much lower compared to No Pep liposome (~80±4.6 to 135±2.3), it was similar to that seen in a previous study (37). Cryo-TEM confirmed that liposome structure was not altered. Lastly, AZ7379 retention was evaluated under physiologic conditions by measuring the release of AZ7379 at 37° C. over a 72-hr. period either in saline or 50% fetal bovine serum (FBS). AZ7379 was released to a much greater extent in saline (60% compared to 20% in FBS), suggesting that both liposomal AZ7379 formulations (No Pep and PTP) would be stable in the blood. These results also suggest that having a peptide-lipid construct in the liposomal formulation does not interfere with the retention of AZ7379.

To confirm PARP inhibition, double stranded-DNA (dsDNA) breaks were quantified by immunostaining for γ-H2AX, a biomarker for double stranded DNA breaks. PTP AZ7379 treated OVCAR8 cells had 35% of nuclear area positive for γ-H2AX, compared to 18% for free AZ7379, and <1% for untreated cells. PARP inhibition in OVCAR8 cells also resulted in trapping of PARP-1 on chromatin. This phenomenon was observed with both free AZ7379 and PTP AZ7379 treated OVCAR8 cells.

Figure 5B:
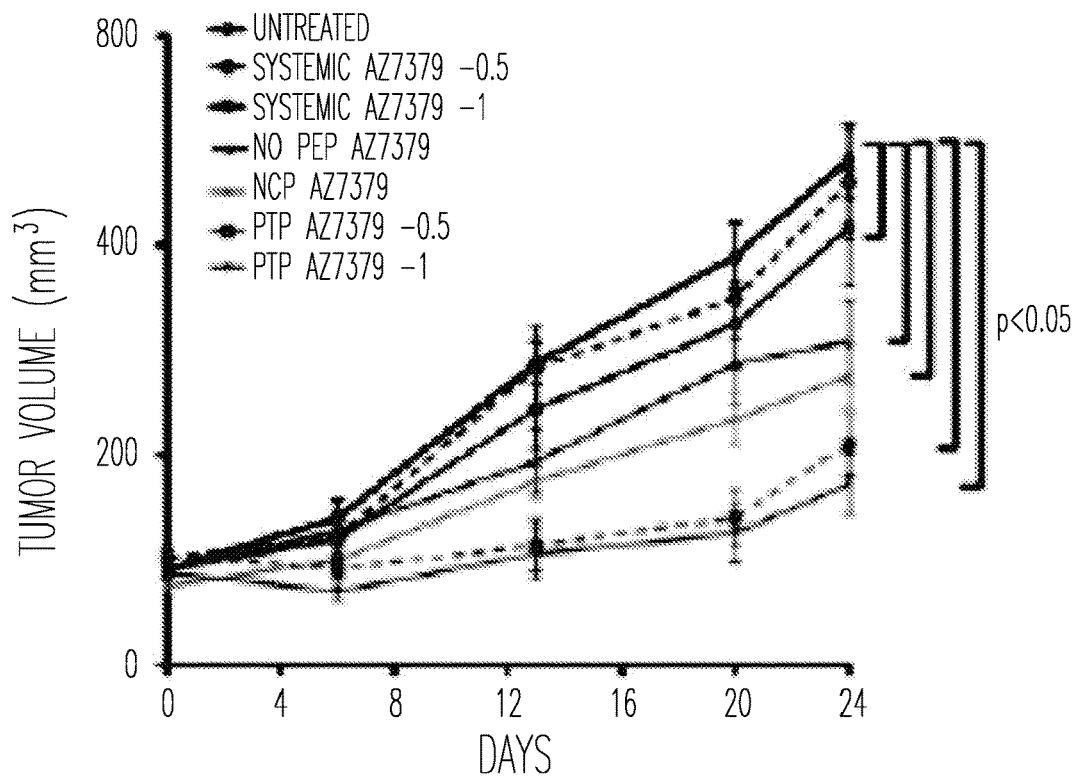
Figure 5C:
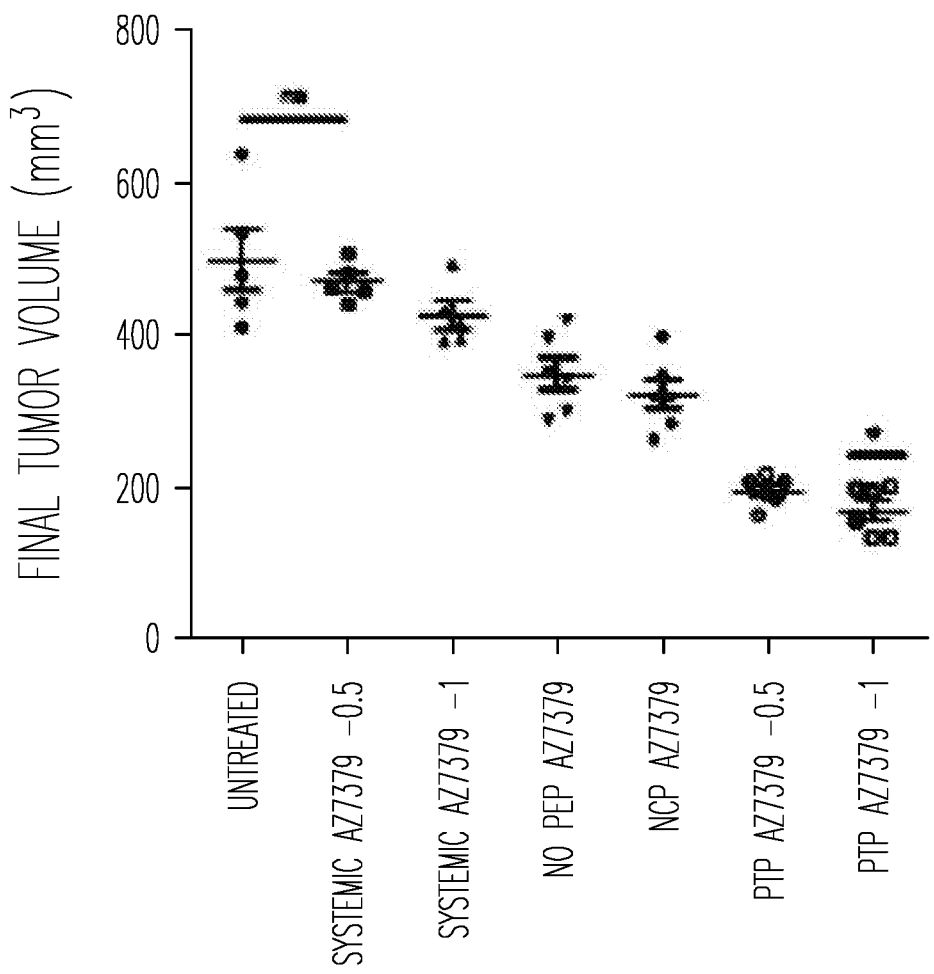
Figures 7B, 7C:
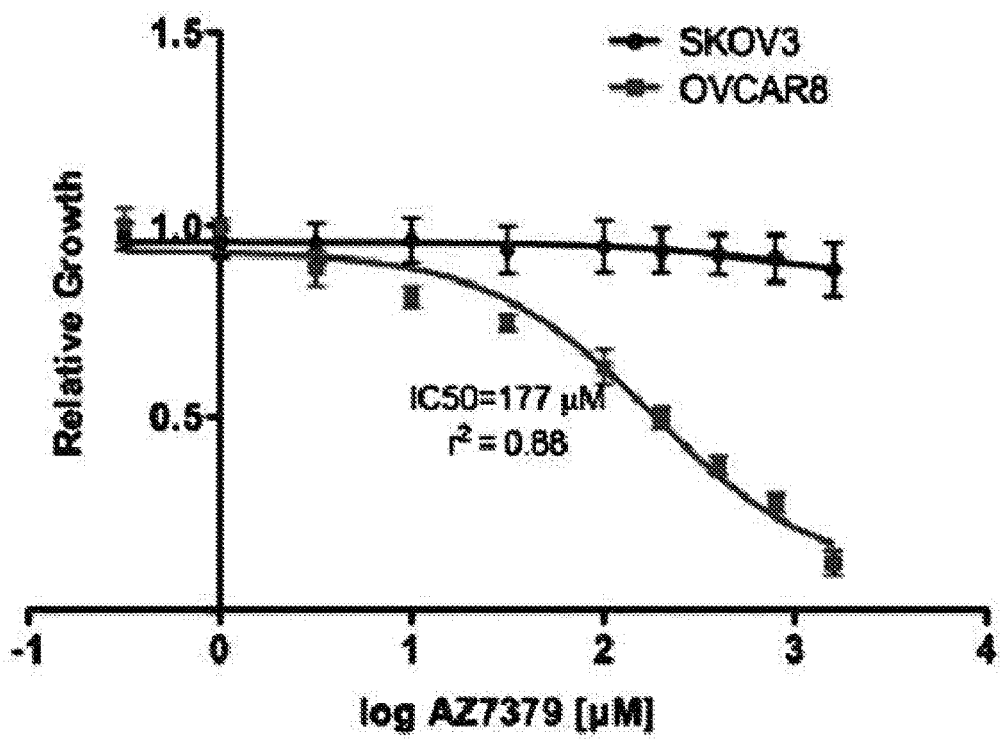

PTP Liposomal Delivery of AZ7379 Inhibits PARP Activity and Elicits Anti-Tumor Effects To determine therapeutic efficacy of the AZ7379 PTP liposome formulation, OVCAR8 tumor outgrowth was compared during seven treatment regimens: 1. untreated, 2. systemic AZ7379-0.5 (0.5 mol/Kg/gavage), 3. systemic AZ7379-1 (1 µmol/Kg/gavage), 4. No Pep AZ7379 (1.5 µmol/Kg/injection) (0.25 mg lipid/injection), 5. NCP AZ7379 (1 µmol/Kg/injection) (0.25 mg lipid/injection), 6. PTP AZ7379-0.5 (0.75 µmol/Kg/injection) (0.12 mg lipid/injection), 7. PTP AZ7379-1 (1.5 µmol/Kg/injection) (0.25 mg lipid/injection) (FIG. 5A). Groups 1,3,4,5,7 received 3 µmol/Kg and groups 2 and 6 received 1.5 µmol/Kg over a 7-day period. A free AZ7379 was delivered via oral gavage every other day based on previous experiments that determined pharmacokinetics and optimal dosing (37). In that study, free AZ7379 was administered at doses 1, 5 and 25 mol/Kg without any apparent adverse effects. As shown in FIG. 7B, the blood half-life of AZ7379 in mice is 55 min when delivered orally compared to 3 min when delivered via tail vein injection. Thus, oral delivery was selected to avoid rapid systemic clearance, consistent with clinical applications where PARP inhibitors are typically administered orally (12,17). Tumor volume was measured every week out to 24 days, at which time the tumors were removed for additional analyses. The data revealed that all liposomal formulations reduced tumor outgrowth to a greater extent than systemic drug delivery, indicating the contribution of the enhanced permeability and retention (EPR) effect to liposomal drug delivery (FIG. 5B) (38-40). Notably, it was found that tumors in PTP liposome-treated animals (groups 6&7) were significantly smaller than those in the other two liposome treated cohorts, indicating that the presence of the PTP targeting moiety was having an effect above background liposome EPR (FIG. 5C). Systemic AZ7379 at 0.5 mol/Kg was not significantly different from untreated group in terms of tumor growth (FIG. 5B). But PTP AZ7379-0.5 had significantly lower final tumor volume compared to other treatment groups (2.5-fold lower compared to untreated, 2.4-fold lower compared to Systemic AZ7379-0.5, 2.2-fold lower compared to Systemic AZ7379-1, 1.8-fold lower compared to No Pep AZ7379 and 1.6-fold compared to NCP AZ7379) (FIG. 5C). These results suggest that at lower dose of AZ7379, PTP liposomes had much greater anti-tumor effect compared to systemic AZ7379 delivery. Similarly, PTP AZ7379—1 had significantly lower final tumor volume compared to other treatment groups (2.9-fold lower compared to untreated, 2.7-fold lower compared to Systemic AZ7379-0.5, 2.5-fold lower compared to Systemic AZ7379-1, 2-fold lower compared to No Pep AZ7379 and 1.8-fold compared to NCP AZ7379) (FIG. 5C). The body weight of the mice was similar across the untreated and all treated groups, indicating that there were no systemic adverse effects of drug delivery. Additionally, similar in vivo experiments conducted in mice bearing SKOV3 tumors (WT BRCA1/2) were resistant to the effects of AZ7379 on tumor growth, indicating that BRCA1/2 status was a determining factor in therapeutic efficacy.

As a further indicator of pharmacodynamics, the extent of PARP inhibition was measured as a surrogate for the delivery of AZ7379 to the tumor. During the DNA repair process, C-terminus catalytic domain of PARP hydrolyzes NAD+ and attaches Poly (ADP-ribose) (PAR) polymers covalently to proteins. Therefore, PARP activity in tumor cells can be quantified by measuring PAR levels. The PAR+ area in the tumor, as determined by immunofluorescence staining intensity, was 3.6-fold lower in PTP AZ7379-1 compared to untreated controls (group 1), 3.4-fold lower compared to Systemic AZ7379-0.5 (group 2), 2.8-fold lower compared to systemic AZ7379-1 (group 3), 2.3-fold lower compared to No Pep/NCP liposomes (groups 4 and 5), and 1.4-fold lower compared to PTP AZ7379-0.5 (group 6). Similarly, immunoblot detection of PAR in tumor lysate preparations showed PTP AZ7379-1 resulted in a 24-fold lower PAR/actin ratio compared to untreated animals (group 1), 21-fold lower compared to Systemic AZ7379-0.5 (group 2), 17-fold lower compared to Systemic AZ7379-1 (group 3), 12-fold lower compared to No Pep/NCP liposomes (Groups 4 and 5), and 3-fold lower compared to PTP AZ7379-0.5 (group 6). Additionally, tumor volumes displayed strong correlation with PAR expression as determined by immunofluorescence ($r^2$=0.93, P=0.0004) and immunoblot ($r^2$=0.97, P=0.0001).

Figure 6A:
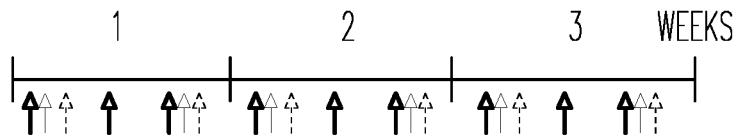
FIGS. 6A-F. PTP liposomes delay tumor growth of OVCAR8 cells expressing iRFP. A) Experimental design for measuring PD following AZ7379 delivery. There were 4 groups—1. Untreated (n=6), 2. Systemic AZ7379 (n=6), 3. No Pep AZ7379 (n=6), 4. PTP liposomes AZ7379 (n=6). Systemic AZ7379 was delivered three times a week by oral gavage and liposomal groups—3 &4 were delivered twice a week via tail vein injections. B) FMT images of mice from different treatment groups at days 2, 12, and 22 after treatment. C) Tumor volume was measured every week following treatment by imaging the mice via FMT and plotted over time to determine the efficacy of each treatment ($p<0.05$). D) Ex vivo FMT images of organs after 3 weeks of treatment. iRFP fluorescence was normalized to the weight of the organs and represented as picomoles of iRFP per gram tissue. Tumor burden included tumor isolated from the omentum and diaphragm which are the major regions where tumor mass was observed. E) PAR and actin were quantified from tumor lysates by Western blot. The Western blot images represents lysates from 3 animals of each group chosen randomly from this study. F) PAR expression was normalized to actin expression in the same lysates/blot. (* represents $p<0.05$).
Figure 6B:
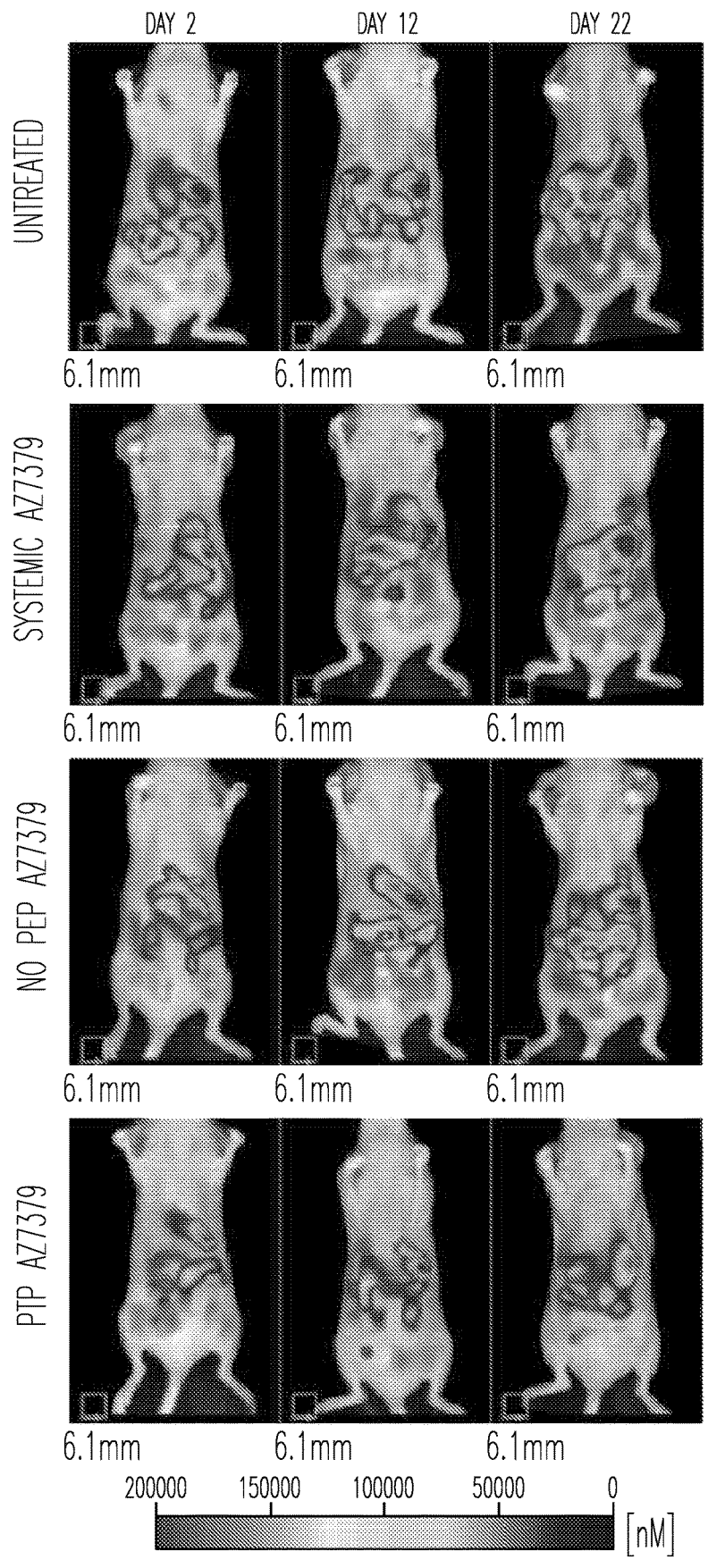

Intraperitoneal injections of ovarian tumor cells into nude mice in many aspects resemble late stage ovarian cancer where extensive peritoneal dissemination and the development of ascites is observed. To assess the efficacy and toxicity of PTP liposomes under these conditions, OVCAR8 that express iRFP720 were injected into the peritoneal cavity and imaged via FMT one-week post injection for tumor growth. The mice were randomized into four treatment groups (n=6 mice/group): 1. untreated control, 2. systemic AZ7379, 3. No Pep AZ7379, and 4. PTP AZ7379 (FIG. 6B).

Figure 6C:
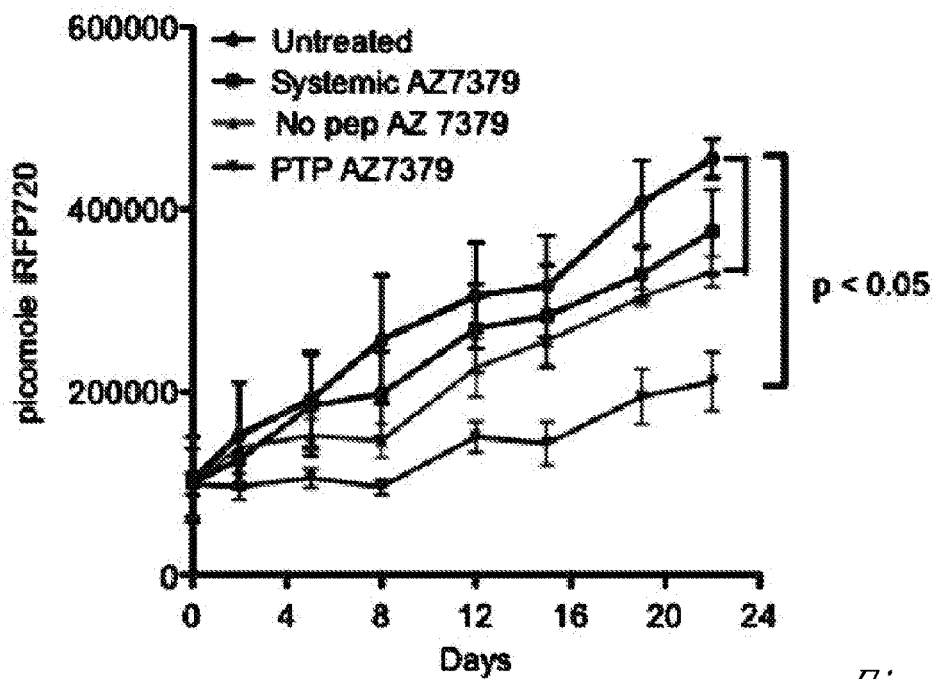
Figure 6D:
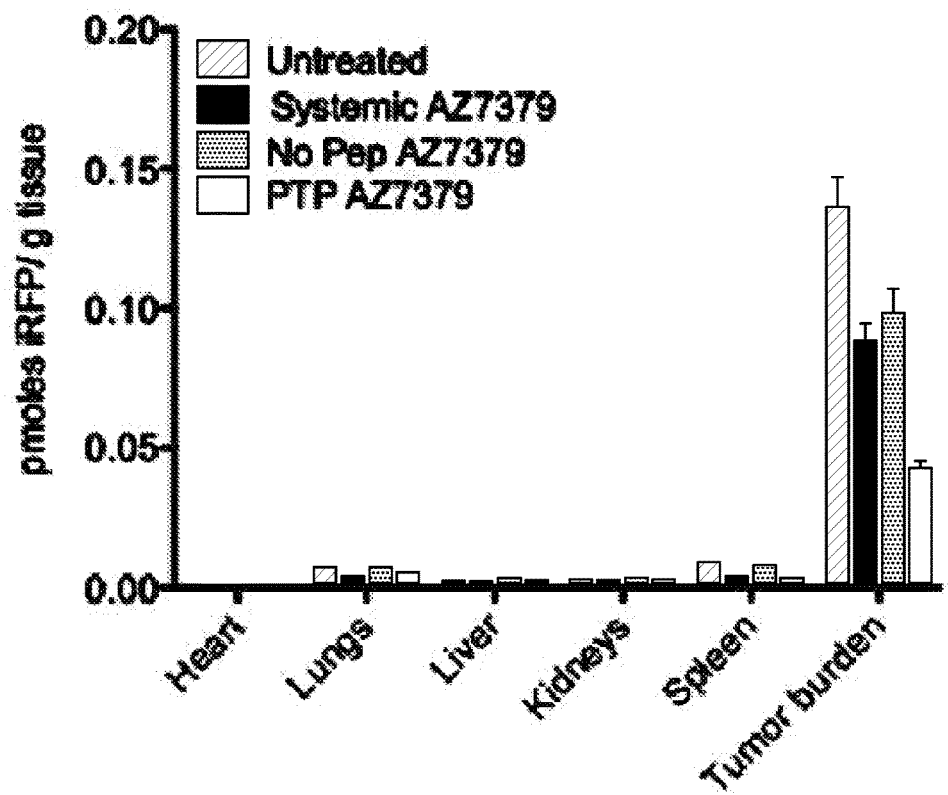
Figure 6E:
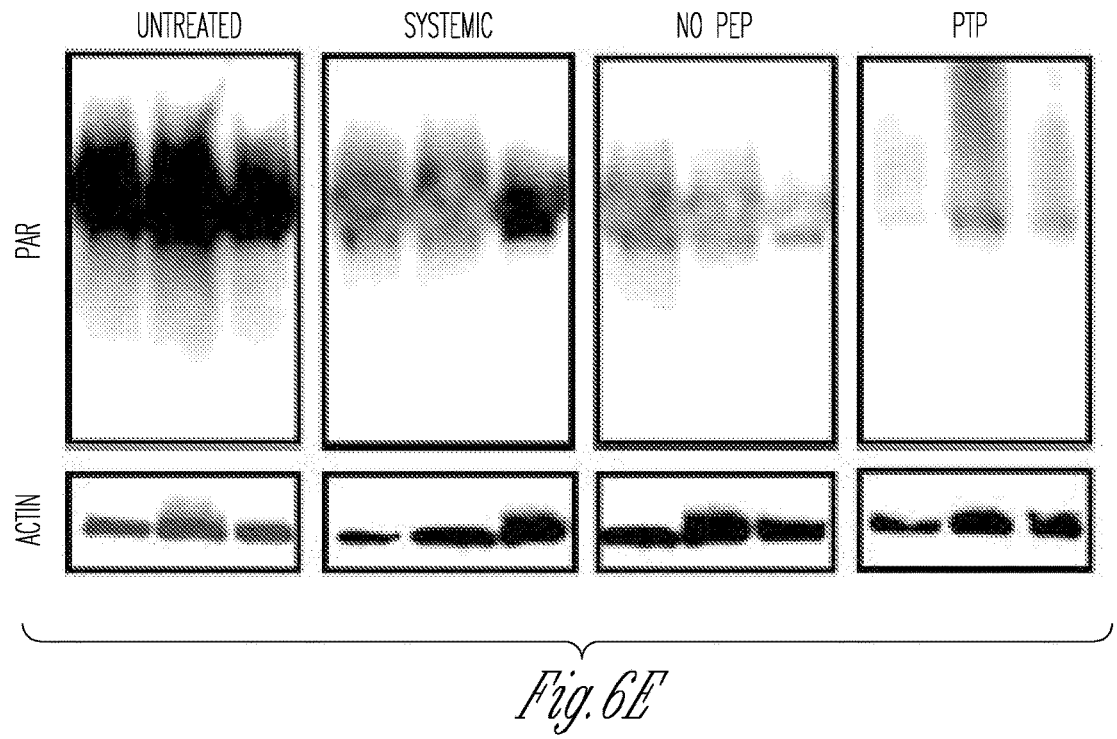
Figure 6F:
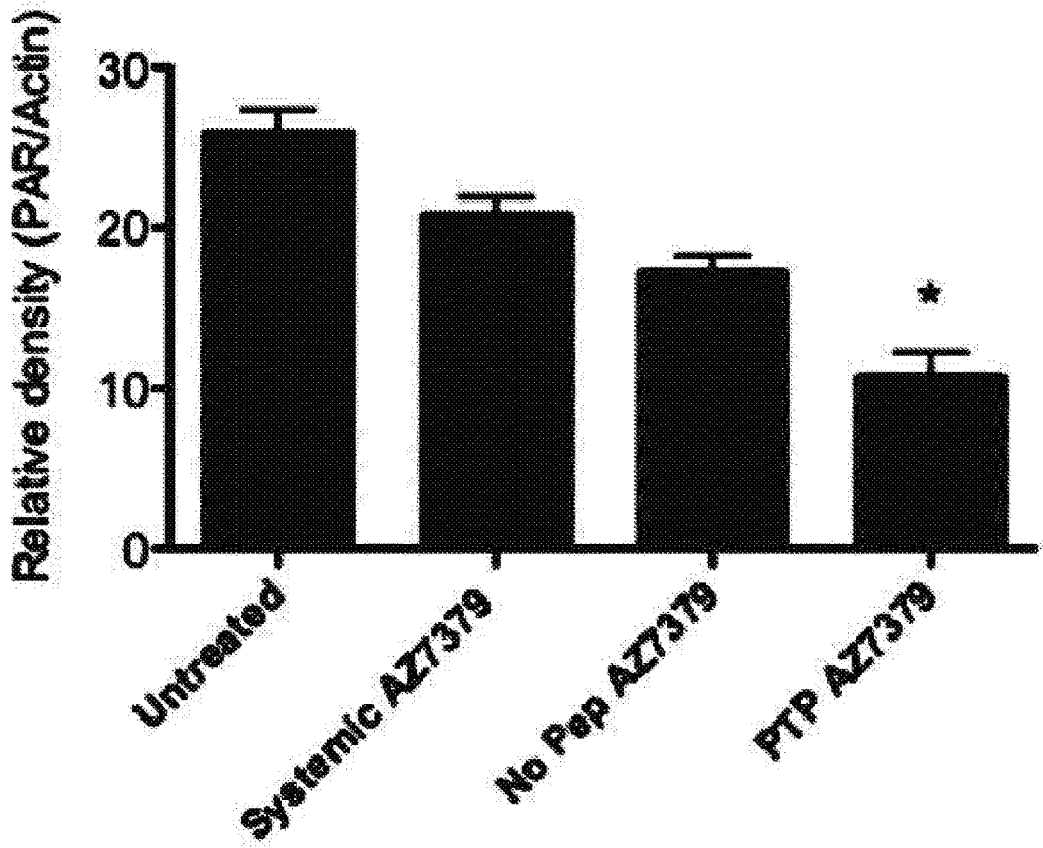

Systemic AZ7379 was performed 3 times a week via oral gavage and liposomes (No Pep and PTP) were delivered via tail vein injections 2 times a week. The total amount of drug given per week across all delivery platforms was kept constant. Mice were imaged twice a week using FMT and tumor growth for all groups was plotted over time (FIG. 6A, C). PTP liposomes treated animals had delayed tumor growth compared to other treatment groups with a final tumor volume that was 2-fold lower compared to untreated control group (455,581 vs. 211,884), 1.7-fold lower compared to systemic AZ7379 treated group (375,894 vs. 211, 884) and 1.6-fold lower compared to No Pep AZ7379 treated group (331,821 vs. 211,884) (FIG. 6C). The body weight of the mice was similar across the untreated and all treated groups, indicating that there were no systemic adverse effects of drug delivery. Upon necropsy, organs were removed and scanned to determine the presence of iRFP OVCAR8 cells (FIG. 6D). It was observed that major tumor mass was associated with the omentum followed by other organs including liver, diaphragm, intestine, reproductive tract, pancreas, and kidneys. The amount of iRFP fluorescence associated with each organ was normalized to tissue weight and represented in FIG. 6D. Tumor burden associated with omentum and diaphragm had the highest iRFP fluorescence per gram tissue compared to other tissues (FIG. 6D). Tumors were homogenized and lysed, amount of PAR in the tumor was assessed by Western blot analysis (FIG. 6E). PTP liposomal delivery of AZ7379 resulted in a 2.4-fold lower PAR/actin ratio compared to untreated animals (group 1), 1.9-fold lower compared to Systemic AZ7379 (Group 2) and 1.6-fold lower compared to No Pep liposomes (FIG. 6E, F).

PTP liposomal delivery of AZ7379 resulted in a 1.7-fold fewer tumor nodules compared to untreated animals (Group 1), 1.6-fold fewer compared to Systemic AZ7379 (group 2) and 1.4-fold lower compared to No Pep liposomes. In order to detect any potential drug toxicity, blood was collected at the end of the treatment period and liver function was evaluated by measuring serum levels of alanine aminotransferase (ALT) and aspartate aminotransferase (AST). There was no significant difference in the serum levels of ALT (42-48 mUnits/mL) or AST (46-54 mUnits/mL) among the treatment groups. Flow cytometry analysis was also performed on blood cells to determine total myeloid lineage cells (% CD11b+ of the CD45+ population), cells that comprise neutrophils/granulocyte subset of myeloid derived suppressor cells (MDSCs) (Ly6G+ population of CD45+ CD11b+ cells), and monocytes (LY6C+ and Ly6C-populations of CD45+CD11b+Ly6G-cells). It was observed that there was no significant difference in total percentage of myeloid cells among the 4 groups. Similarly, there was no difference in the percentage of Ly6G+ myeloid cells and monocytes. This indicates that PARP inhibition with free or liposomal AZ7379 at 3 μmol/Kg/week over the three-week treatment period did not alter myeloid cell populations in the blood. Taken together, these results indicate that PTP liposomes mediated delivery of the PARP inhibitor AZ7379 provides a superior platform for drug delivery compared to systemic and No Pep liposome delivery. Two outcomes were demonstrated: first, that PARP inhibition in the tumor was enhanced with the PTP liposomes, and second, that tumor volume was reduced in these mice compared to other groups. More broadly, these results strengthen the concept that targeted liposomal delivery can reduce the frequency of therapeutic dosing while at the same time increase the efficacy of the PARP inhibition.

Discussion

The current work using a PTP liposomal AZ7379 formulation provides evidence that the individual powers of pharmacogenomics and oncoproteomics can be magnified when combined. The methodology involved using pharmacogenomics data to select the model, BRCA1/2 deficient OVCAR8 cells, and the PARP inhibitor, AZ7379, that was utilized in the study. The oncoproteomic elements were then systematically defined, that plectin is highly expressed in more advanced human ovarian cancer and that it is expressed on the cell surface. When combined with oncoproteomic data from previous work demonstrating that the PTP peptide specifically targets cell surface plectin, a foundation upon which to test the hypothesis: that targeted liposomes encapsulating a PARP inhibitor would increase drug delivery to the tumor. As a final component, a protocol to generate liposomes was developed and optimized that showed little loss of initial lipid content, were uniform in size, retained drug at a dose that was therapeutically effective, maintained structural integrity, and were stable under physiological conditions. Following this approach, it was demonstrated that AZ7379 encapsulated in PTP liposomes increased PARP inhibition in OVCAR8 tumors (subcutaneous & intraperitoneal) over No Pep/NCP liposomes, and that tumor growth was reduced under these conditions. The long-term use of PARP inhibitors can lead to resistance, often attributed to changes in the DNA damage response mediated by secondary mutations in BRCA genes or changes in cellular response to PARP inhibitors like altered ATP-binding cassette (ABC) transporters that reduce the efficacy of PARP-1 inhibitors (41,42). Others have shown that NF-κB inhibitors were effective in overcoming PARP-1 inhibitor resistance (43).

Very promising is that we now have an adaptable therapeutic platform, incorporating pharmacogenomics, oncoproteomics, and liposome-mediated delivery. Optimization of each component in relation to the others plays a rold in success. A feature of the method and the goal of any therapeutic is cell-specific delivery. Relating this to the study, the development of PARP inhibitors to treat cancers with BRCA-like mutations displays the strengths of the pharmacogenomics, while the adverse effects in healthy organs following clinical application displays its weaknesses. The most concerning adverse effects associated with PARP inhibition are myelodysplastic syndrome and acute myeloid leukemia. Under these conditions, the patients are unable to replenish blood cells, to the point of death in some cases. Although liposomes accumulate in the liver, in vivo toxicity studies suggested that liposomal AZ7379 did not cause measurable liver damage as seen with unaltered serum ALT, AST levels.

Furthermore, PTP AZ7379 formulation could potentially be used to enhance efficacy in other cancer types that harbor cell surface plectin/BRCA deficient cancer cells, including several head and neck squamous cell carcinomas (HNSCC) and pancreatic cancer. In a recently concluded clinical study, Rucaparib (PARP inhibitor) showed benefit in 36% of pancreatic cancer patients (P4,45). In HNSCC, where BRCA1/2 and BRCA-like mutations contribute to about >10% of cases (46-49).

Even without targeting, No Pep liposomal AZ7379 formulations like those described here can be used to effectively treat BRCA—like mutations that contribute to about 13% of all tumors (49). Thus, a liposomal formulation incorporating a PARP inhibitor holds promise for a number of cancer treatment strategies.

Additionally, this platform can be expanded to deliver chemotherapeutic drugs at prescribed stages of cancer treatment either as a mono or combinatorial therapy. For example, the presence of plectin can be exploited to deliver liposomes encapsulated with carboplatin or doxorubicin, among other frontline drugs. Remote loading was chosen as the method for encapsulating PARP inhibitors (Olaparib, AZ7379, AZ3598, and AZ9594) as it is a highly efficient and simple procedure. Computational modeling and various experimental methods have already been explored that match suitable and optimize remote loading techniques with the properties of any given drug (50-52). The clinical applicability of any liposomal formulation depends on the stability upon long-term storage and in vivo following administration. In this case, storage of PTP liposomes at 4° C. for 3 months resulted in only a loss of 10% AZ7379 (data not shown) and the loss occurred during the first 24h upon storage. The anti-tumor effects seen in the studies confirm in vivo stability of PTP liposomes, and they also indicate successful uptake of liposomes by cell surface plectin+ OVCAR8 cells followed by release of AZ7379 and inhibition of PARP. The current AZ7379 formulation can be further optimized by minimizing the loss of lipids during remote loading process, which can likely be addressed through identification of the right packing material for size exclusion chromatography. Even with the loss of lipid during the size exclusion process, a loading of 80 µg of AZ7379 per mg of lipid for peptide conjugated liposomes was achieved. Although this is lower than what has been previously reported for doxorubicin in unlabeled liposomes (200 µg drug per mg of lipid) (40), it does highlight the therapeutic strength of the formulation, as PARP inhibition and reduced tumor growth were achieved at these levels.

CONCLUSIONS

This work serves as a model system for developing effective anti-tumor therapies against cancer with specific genetic and protein expression profiles. Given that this approach is based on the integration of pharmacogenomics and oncoproteomic information, it is predicted that these two rapidly expanding and clinically accepted fields will unveil a new field of diseases that can be treated more efficaciously with reduced deleterious side effects to the patients. Targeted drug delivery thus serves as a bridge between the -omics technologies which can further stream precision cancer medicine.

BIBLIOGRAPHY

1. Hofree M, Shen J P, Carter H, Gross A, Ideker T. Network-based stratification of tumor mutations. Nat Methods. 2013; 10(11):1108-15.
2. Cho W C. Contribution of oncoproteomics to cancer biomarker discovery. Mol Cancer. 2007; 6:25.
3. Meani F, Pecorelli S, Liotta L, Petricoin E F. Clinical application of proteomics in ovarian cancer prevention and treatment. Mol Diagn Ther. 2009; 13(5):297-311.
4. Kelly K A, Bardeesy N, Anbazhagan R, Gurumurthy S, Berger J, Alencar H, et al. Targeted nanoparticles for imaging incipient pancreatic ductal adenocarcinoma. PLoS Med. 2008; 5(4): e85.
5. Bausch D, Thomas S, Mino-Kenudson M, Castillo C F, Bauer T W, Williams M, et al. Plectin-1 as a novel biomarker for pancreatic cancer. Clin Cancer Res. 2011; 17(2):302-9.
6. Reynolds F, Panneer N, Tutino C M, Wu M, Skrabal W R, Moskaluk C, et al. A functional proteomic method for biomarker discovery. PLoS One. 2011; 6(7): e22471.
7. Tutt A, Ashworth A. The relationship between the roles of BRCA genes in DNA repair and cancer predisposition. Trends Mol Med. 2002; 8(12):571-6.
8. Integrated Genomic Analyses of Ovarian Carcinoma. Nature. 2011; 474(7353):609-15.
9. Bolton K L, Chenevix-Trench G, Goh C, Sadetzki S, Ramus S J, Karlan B Y, et al. Association between BRCA1 and BRCA2 mutations and survival in women with invasive epithelial ovarian cancer. JAMA. 2012; 307(4):382-90.
10. Konecny G E, Wang C, Hamidi H, Winterhoff B, Kalli K R, Dering J, et al. Prognostic and therapeutic relevance of molecular subtypes in high-grade serous ovarian cancer. J Natl Cancer Inst. 2014; 106(10).
11. Balmaña J, Domchek S M, Tutt A, Garber J E. Stumbling blocks on the path to personalized medicine in breast cancer: the case of PARP inhibitors for BRCA1/2-associated cancers. Cancer Discov. 2011; 1(1):29-34.
12. Ledermann J, Harter P, Gourley C, Friedlander M, Vergote I, Rustin G, et al. Olaparib maintenance therapy in patients with platinum-sensitive relapsed serous ovarian cancer: a preplanned retrospective analysis of outcomes by BRCA status in a randomized phase 2 trial. Lancet Oncol. 2014; 15(8):852-61.
13. [Internet]. https://www.fda.gov/newsevents/newsroom/comunicadosdeprensa/ucm427584.htm
14. [Internet]. Research C for DE and. Approved Drugs—Rucaparib. https://www.fda.gov/Drugs/InformationOnDrugs/ApprovedDrugs/ucm533891.htm
15. [Internet]. Research C for DE and. Approved Drugs—Niraparib (ZEJULA). https://www.fda.gov/Drugs/InformationOnDrugs/ApprovedDrugs/ucm548487.htm
16. Kristeleit R, Shapira-Frommer R, Burris H, Patel M R, Lorusso P M, Oza A M, et al. 882PDphase 1/2 study of oral rucaparib: updated phase I and preliminary phase 2 results. Ann Oncol. 2014; 25(suppl 4):307-8.
17. Kristeleit R S, Burris H A, LoRusso P, Patel M R, Asghar U S, El-Khouly F, et al. Phase 1/2 study of oral rucaparib: Final phase 1 results. J Clin Oncol. 2014; 32(suppl 15):2573-2573.
18. Kristeleit R, Shapiro G I, Burris H A, Oza A M, LoRusso P, Patel M R, et al. A Phase I-II Study of the Oral PARP Inhibitor Rucaparib in Patients with Germline BRCA1/2-Mutated Ovarian Carcinoma or Other Solid Tumors. Clin Cancer Res. 2017; 23(15): 4095-106.
19. Shapiro G, Kristeleit R, Middleton M, Burris H, Molife L R, Evans J, et al. Abstract A218: Pharmacokinetics of orally administered rucaparib in patients with advanced solid tumors. Mol Cancer Ther. 2013; 12: A218-A218.
20. Ricks T K, Chiu H J, Ison G, Kim G, McKee A E, Kluetz P, et al. Successes and Challenges of PARP Inhibitors in Cancer Therapy. Front Oncol. 2015; 5:222
21. Allen T M, Cullis P R. Liposomal drug delivery systems: From concept to clinical applications. Adv. Drug Deliv Rev. 2013; 65(1):36-48.
22. Song G, Wu H, Yoshino K, Zamboni W C. Factors affecting the pharmacokinetics and pharmacodynamics of liposomal drugs. J Liposome Res. 2012; 22(3):177-92.

23. Torchilin V P. Recent advances with liposomes as pharmaceutical carriers. Nat Rev Drug Discov. 2005; 4(2): 145-60.
24. cagda M, Sezer A D, Bucak S. Liposomes as Potential Drug Carrier Systems for Drug Delivery. London UK: IntechOpen publishers; 2014.
25. Caster J M, Sethi M, Kowalczyk S, Wang E, Tian X, Nabeel Hyder S, et al. Nanoparticle delivery of chemosensitizers improve chemotherapy efficacy without incurring additional toxicity. Nanoscale. 2015 Feb. 14; 7(6): 2805-11.
26. van de Ven A L, Tangutoori S, Baldwin P, Qiao J, Gharagouzloo C, Seitzer N, et al. Nanoformulation of Olaparib Amplifies PARP Inhibition and Sensitizes PTEN/TP53—Deficient Prostate Cancer to Radiation. Mol Cancer Ther. 2017; 16(7):1279-89.
27. Chang D K, Li P C, Lu R M, Jane W N, Wu H C. Peptide-mediated liposomal Doxorubicin enhances drug delivery efficiency and therapeutic efficacy in animal models. PLoS One. 2013; 8(12): e83239.
28. Wu C H, Kuo Y H, Hong R L, Wu HC. α-Enolase-binding peptide enhances drug delivery efficiency and therapeutic efficacy against colorectal cancer. Sci Transl Med. 2015; 7(290):290ra91.
29. Dasa S, Suzuki R, Mugler E, Chen L, Jansson-Löfmark R, Michaelsson E, et al. Evaluation of Pharmacokinetic and Pharmacodynamic Profiles of Liposomes for the Cell Type-Specific Delivery of Small Molecule Drugs. Nanomedicine. 2017; pii: S1549.
30. King A, Ndifon C, Lui S, Widdows K, Kotamraju V R, Agemy L, et al. Tumor-homing peptides as tools for targeted delivery of payloads to the placenta. Sci Adv. 2016; 2(5): e1600349.
31. Fosgerau K, Hoffmann T. Peptide therapeutics: current status and future directions. Drug Discov Today. 2015; 20(1):122-8.
32. Uhlig T, Kyprianou T, Martinelli F G, Oppici C A, Heiligers D, Hills D, et al. The emergence of peptides in the pharmaceutical business: From exploration to exploitation. EuPA Open Proteomics. 2014; 4:58-69.
33. Konkalmatt P R, Deng D, Thomas S, Wu M T, Logsdon C D, French B A, et al. Plectin-1 Targeted AAV Vector for the Molecular Imaging of Pancreatic Cancer. Front Oncol. 2013; 3:84.
34. [Internet]. Leung K. (111) In-Tetrameric Plectin-1 targeting peptide (4(βAKTLLPTP-GGS(PEG5000)) KKK-(111) In-DOTA-βA-NH2). In: Molecular Imaging and Contrast Agent Database (MICAD) 2004. http://www.ncbi.nlm.nih.gov/books/NBK54202/
35. Jazaeri A A, Bryant J L, Park H, Li H, Dahiya N, Stoler M H, et al. Molecular Requirements for Transformation of Fallopian Tube Epithelial Cells into Serous Carcinoma. Neoplasia. 2011; 13(10):899-911.
36. Vasquez K O, Casavant C, Peterson J D. Quantitative whole body biodistribution of fluorescent-labeled agents by non-invasive tomographic imaging. PLoS One. 2011; 6(6): e20594.
37. Dasa S, Suzuki R, Gutknecht M, Brinton L T, Tian Y, Michaelsson E, et al. Development of target-specific liposomes for delivering small molecule drugs after reperfused myocardial infarction. J Control Release. 2015; 220(Pt A):556-67.
38. Noble G T, Stefanick J F, Ashley J D, Kiziltepe T, Bilgicer B. Ligand-targeted liposome design: challenges and fundamental considerations. Trends Biotechnol. 2014; 32(1):32-45.
39. Nichols J W, Bae Y H. EPR: Evidence and fallacy. J Control Release. 2014; 190:451-64.
40. Barenholz Y. Doxil®—the first FDA-approved nano-drug: lessons learned. J Control Release. 2012; 160(2): 117-34.
41. Lord C J, Ashworth A. Mechanisms of resistance to therapies targeting BRCA-mutant cancers. Nat Med. 2013 November; 19(11):1381-8.
42. Yalon M, Tuval-Kochen L, Castel D, Moshe I, Mazal I, Cohen O, et al. Overcoming Resistance of Cancer Cells to PARP-1 Inhibitors with Three Different Drug Combinations. PLoS One. 2016 May 19; 11(5): e0155711.
43. Nakagawa Y, Sedukhina A S, Okamoto N, Nagasawa S, Suzuki N, Ohta T, et al. NF-κB signaling mediates acquired resistance after PARP inhibition. Oncotarget. 2015 Feb. 28; 6(6):3825-39.
44. Domchek S M, Hendifar A E, McWilliams R R, Geva R, Epelbaum R, Biankin A, et al. RUCAPANC: An open-label, phase 2 trial of the PARP inhibitor rucaparib in patients (pts) with pancreatic cancer (PC) and a known deleterious germline or somatic BRCA mutation. J Clin Oncol. 2016; 34(suppl 15) 4110.
45. Syed Y Y. Rucaparib: First Global Approval. Drugs. 2017 April; 77(5):585-92.
46. Feldman R, Gatalica Z, Knezetic J, Reddy S, Nathan C-A, Javadi N, et al. Molecular profiling of head and neck squamous cell carcinoma. Head Neck. 2016; 38(S1): E1625-38.
47. Heitmann J, Geeleher P, Zuo Z, Weichselbaum R R, Vokes E E, Fetscher S, et al. Poly (ADP-ribose) polymerase inhibitor efficacy in head and neck cancer. Oral Oncol. 2014; 50(9):825-31.
48. Heeke A, baker T, Lynce F, Pishvaian M. Meeting Library|Prevalence of Homologous Recombination Deficiency (HRD) Among All Tumor Types. J Clin Oncol. 2017; 35: (Suppl 15) 1502.
49. Cern A, Marcus D, Tropsha A, Barenholz Y, Goldblum A. New drug candidates for liposomal delivery identified by computer modeling of liposomes' remote loading and leakage. J Control Release. 2017; 252:18-27.
50. Zucker D, Marcus D, Barenholz Y, Goldblum A. Liposome drugs' loading efficiency: a working model based on loading conditions and drug's physicochemical properties. J Control Release. 2009; 139(1):73-80.
51. Barenholz Y. Amphipathic Weak Base Loading into Preformed Liposomes Having a Transmembrane Ammonium Ion Gradient. In: Gregoriadis G, ed. Liposome Technology, Volume II. Entrapment of drugs and other materials into liposomes, third edition. Boca Raton, USA: CRC press; 2006: 1-25
52. Szoka F, Papahadjopoulos D. Procedure for preparation of liposomes with large internal aqueous space and high capture by reverse-phase evaporation. Proc Natl Acad Sci USA. 1978; 75(9):4194-8.

All publications, patents, and patent applications, Genbank sequences, websites and other published materials referred to throughout the disclosure herein are herein incorporated by reference to the same extent as if each individual publication, patent, or patent application, Genbank sequences, websites and other published materials was specifically and individually indicated to be incorporated by reference. In the event that the definition of a term incorporated by reference conflicts with a term defined herein, this specification shall control.

What is claimed is:

1. A method to treat cancer comprising administrating to a subject in need thereof an effective amount of a composition comprising a Plectin Targeted Peptide (PTP) conjugated nanoparticle, wherein the PTP is on the surface of the nanoparticle and the nanoparticle encapsulates a payload, wherein the payload is passively loaded, wherein cells of the cancer have mutated BRCA1/2 and express plectin.

2. The method of claim 1, wherein the cancer is ovarian cancer.

3. A method to decrease tumor volume comprising administering to a subject in need thereof an effective amount of a composition comprising a Plectin Targeted Peptide (PTP) conjugated nanoparticle, wherein the PTP is on the surface of the nanoparticle and the nanoparticle encapsulates a payload, wherein the payload is passively loaded, wherein cells of the tumor have mutated BRCA1/2 and express plectin.

4. The method of claim 1, wherein the cancer is head and neck squamous cell carcinomas (HNSCC) or pancreatic cancer.

5. The composition of claim 1, wherein the PTP is any one of SEQ ID NOs: 1-24.

6. The composition of claim 1, wherein the PTP is SEQ ID NO: 1.

7. The composition of claim 1, wherein the nanoparticle is a liposome.

8. The composition of claim 1, wherein the payload is an anticancer compound.

9. The composition of claim 1, wherein the payload is carboplatin, doxorubicin or paclitaxel.

10. The composition of claim 1, wherein the payload is PARP inhibitor.

11. The composition of claim 1, wherein the payload is PARP inhibitor AZ7379.

\* \* \* \* \*